US012408856B1

United States Patent
Kumar et al.

(10) Patent No.: US 12,408,856 B1
(45) Date of Patent: *Sep. 9, 2025

(54) DEVICE FEATURES AND DESIGN ELEMENTS FOR LONG-TERM ADHESION

(71) Applicant: iRhythm Technologies, Inc., San Francisco, CA (US)

(72) Inventors: Uday N. Kumar, San Francisco, CA (US); Peter H. Livingston, San Francisco, CA (US); Mark J. Day, San Francisco, CA (US); Shena Hae Park, San Francisco, CA (US); William F. Willis, San Francisco, CA (US); William H. Righter, San Francisco, CA (US)

(73) Assignee: iRhythm Technologies, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/212,547

(22) Filed: May 19, 2025

Related U.S. Application Data

(63) Continuation of application No. 18/806,584, filed on Aug. 15, 2024, now Pat. No. 12,303,277, which is a
(Continued)

(51) Int. Cl.
*A61B 5/05* (2021.01)
*A61B 5/00* (2006.01)
(Continued)

(52) U.S. Cl.
CPC ............... *A61B 5/282* (2021.01); *A61B 5/25* (2021.01); *A61B 5/259* (2021.01); *A61B 5/291* (2021.01);
(Continued)

(58) Field of Classification Search
CPC ............... A61B 5/0006; A61B 5/1118; A61B 5/6833; A61B 5/282; A61B 2560/0412;
(Continued)

(56) References Cited

U.S. PATENT DOCUMENTS

| 1,497,079 A | 6/1924 | Gullborg |
| 2,179,922 A | 11/1939 | Dana |

(Continued)

FOREIGN PATENT DOCUMENTS

| AU | 2011252998 | 8/2015 |
| AU | 2014209376 | 6/2017 |

(Continued)

OTHER PUBLICATIONS

US 8,750,980 B2, 06/2014, Katra et al. (withdrawn)
(Continued)

*Primary Examiner* — Joseph A Stoklosa
*Assistant Examiner* — Brian M Antiskay
(74) *Attorney, Agent, or Firm* — Knobbe, Martens, Olson & Bear, LLP

(57) ABSTRACT

An electronic device for long-term adhesion to a mammal includes a housing with an electronic component. The electronic device may include a first wing and a second wing, each being integrally formed with the housing. An electrode is positioned on a bottom surface of each of the wings, the electrodes electrically connected to the electronic component. An adhesive layer is provided for adhesion to a surface of the mammal. The adhesive layer may cover a portion of the bottom surfaces of the wings but generally does not cover the electrode or a bottom surface of the housing. A method of applying an electronic device to a mammal includes removing first and second adhesive covers
(Continued)

from first and second wings of the electronic device to expose an electrode and an adhesive coated on a bottom surface of each wing.

20 Claims, 11 Drawing Sheets

Related U.S. Application Data continuation of application No. 17/304,811, filed on Jun. 25, 2021, now Pat. No. 12,133,734, which is a continuation of application No. 16/723,208, filed on Dec. 20, 2019, now Pat. No. 11,141,091, which is a continuation of application No. 16/138,819, filed on Sep. 21, 2018, now Pat. No. 10,517,500, which is a continuation of application No. 15/005,854, filed on Jan. 25, 2016, now Pat. No. 10,405,799, which is a continuation of application No. 13/890,144, filed on May 8, 2013, now Pat. No. 9,241,649, which is a continuation of application No. 13/563,546, filed on Jul. 31, 2012, now Pat. No. 8,538,503, which is a continuation of application No. 13/106,750, filed on May 12, 2011, now Pat. No. 8,560,046.

(60) Provisional application No. 61/334,081, filed on May 12, 2010.

(51) Int. Cl.
*A61B 5/25* (2021.01)
*A61B 5/259* (2021.01)
*A61B 5/282* (2021.01)
*A61B 5/291* (2021.01)
*A61B 5/389* (2021.01)

(52) U.S. Cl.
CPC .......... *A61B 5/6832* (2013.01); *A61B 5/6833* (2013.01); *A61B 5/68335* (2017.08); *A61B 5/389* (2021.01); *A61B 2560/0406* (2013.01); *A61B 2560/0468* (2013.01); *Y10T 156/10* (2015.01)

(58) Field of Classification Search
CPC ......... A61B 5/053; A61B 5/369; A61B 5/308; A61B 5/6804; A61N 1/0492; A61N 1/0476
USPC .................... 600/372, 382–393, 508–509
See application file for complete search history.

(56) References Cited

U.S. PATENT DOCUMENTS

| | | |
|---|---|---|
| 2,201,645 A | 5/1940 | Epner |
| 2,311,060 A | 2/1943 | Lurrain |
| 2,444,552 A | 7/1948 | Sigurd |
| 2,500,840 A | 3/1950 | Lyons |
| 3,215,136 A | 11/1965 | Holter et al. |
| 3,547,107 A | 12/1970 | Chapman et al. |
| 3,697,706 A | 10/1972 | Huggard |
| 3,870,034 A | 3/1975 | James |
| 3,882,853 A | 5/1975 | Gofman |
| 3,911,906 A | 10/1975 | Reinhold |
| 4,023,312 A | 5/1977 | Stickney |
| 4,027,664 A | 6/1977 | Heavner, Jr. et al. |
| 4,082,087 A | 4/1978 | Howson |
| 4,121,573 A | 10/1978 | Crovella et al. |
| 4,123,785 A | 10/1978 | Cherry et al. |
| 4,126,126 A | 11/1978 | Bare |
| 4,202,139 A | 5/1980 | Hong et al. |
| 4,274,419 A | 6/1981 | Tam et al. |
| 4,274,420 A | 6/1981 | Hymes |
| 4,280,507 A | 7/1981 | Rosenberg |
| 4,286,610 A | 9/1981 | Jones |
| 4,333,475 A | 6/1982 | Moreno et al. |
| 4,361,990 A | 12/1982 | Link |
| 4,381,792 A | 5/1983 | Busch |
| 4,438,767 A | 3/1984 | Nelson |
| 4,459,987 A | 7/1984 | Pangburn |
| 4,535,783 A | 8/1985 | Marangoni |
| 4,537,207 A | 8/1985 | Gilhaus |
| 4,572,187 A | 2/1986 | Schetrumpf |
| 4,621,465 A | 11/1986 | Pangburn |
| 4,622,979 A | 11/1986 | Katchis et al. |
| 4,623,206 A | 11/1986 | Fuller |
| 4,658,826 A | 4/1987 | Weaver |
| 4,712,552 A | 12/1987 | Pangburn |
| 4,736,752 A | 4/1988 | Munck et al. |
| 4,763,660 A | 8/1988 | Kroll et al. |
| 4,855,294 A | 8/1989 | Patel |
| 4,925,453 A | 5/1990 | Kannankeril |
| 4,938,228 A | 7/1990 | Righter et al. |
| 4,981,141 A | 1/1991 | Segalowitz |
| 5,003,987 A | 4/1991 | Grinwald |
| 5,027,824 A | 7/1991 | Dougherty et al. |
| 5,082,851 A | 1/1992 | Appelbaum et al. |
| 5,086,778 A | 2/1992 | Mueller et al. |
| 5,191,891 A | 3/1993 | Righter |
| 5,205,295 A | 4/1993 | Del Mar et al. |
| 5,226,425 A | 7/1993 | Righter |
| 5,228,450 A | 7/1993 | Sellers |
| 5,230,119 A | 7/1993 | Woods et al. |
| 5,289,824 A | 3/1994 | Mills et al. |
| 5,305,746 A | 4/1994 | Fendrock |
| 5,309,909 A | 5/1994 | Gadsby |
| 5,328,935 A | 7/1994 | Van Phan |
| 5,365,935 A | 11/1994 | Righter et al. |
| 5,458,141 A | 10/1995 | Neil |
| 5,483,967 A | 1/1996 | Ohtake |
| 5,489,624 A | 2/1996 | Kantner et al. |
| 5,511,548 A | 4/1996 | Riazzi et al. |
| 5,511,553 A | 4/1996 | Segalowitz |
| 5,515,858 A | 5/1996 | Myllymaki |
| 5,536,768 A | 7/1996 | Kantner et al. |
| 5,581,369 A | 12/1996 | Righter et al. |
| 5,626,140 A | 5/1997 | Feldman et al. |
| 5,634,468 A | 6/1997 | Platt et al. |
| 5,645,063 A | 7/1997 | Straka |
| 5,645,068 A | 7/1997 | Mezack et al. |
| 5,730,143 A | 3/1998 | Schwarzberg |
| 5,749,365 A | 5/1998 | Magill |
| 5,749,367 A | 5/1998 | Gamlyn et al. |
| 5,771,524 A | 6/1998 | Woods et al. |
| 5,772,604 A | 6/1998 | Langberg et al. |
| 5,776,072 A | 7/1998 | Hsu et al. |
| 5,881,743 A | 3/1999 | Nadel |
| D408,541 S | 4/1999 | Dunshee et al. |
| 5,916,239 A | 6/1999 | Geddes et al. |
| 5,931,791 A | 8/1999 | Saltzstein et al. |
| 5,941,829 A | 8/1999 | Saltzstein et al. |
| 5,957,854 A | 9/1999 | Besson et al. |
| 5,959,529 A | 9/1999 | Kail |
| 6,013,007 A | 1/2000 | Root et al. |
| 6,032,060 A | 2/2000 | Carim |
| 6,038,464 A | 3/2000 | Axelgaard et al. |
| 6,038,469 A | 3/2000 | Karlsson et al. |
| 6,044,515 A | 4/2000 | Zygmont |
| 6,093,146 A | 7/2000 | Filangeri |
| D429,336 S | 8/2000 | Francis et al. |
| 6,102,856 A | 8/2000 | Groff et al. |
| 6,117,077 A | 9/2000 | Del Mar et al. |
| 6,121,508 A | 9/2000 | Bischof |
| 6,132,371 A | 10/2000 | Dempsey et al. |
| 6,134,480 A | 10/2000 | Minogue |
| 6,136,008 A | 10/2000 | Becker et al. |
| 6,161,036 A | 12/2000 | Matsumura et al. |
| 6,169,915 B1 | 1/2001 | Krumbiegel et al. |
| 6,178,357 B1 | 1/2001 | Gliner et al. |
| 6,200,265 B1 | 3/2001 | Walsh et al. |
| 6,223,080 B1 | 4/2001 | Thompson |
| 6,225,901 B1 | 5/2001 | Kail |

(56) References Cited

U.S. PATENT DOCUMENTS

| | | |
|---|---|---|
| 6,232,366 B1 | 5/2001 | Wang et al. |
| 6,238,338 B1 | 5/2001 | DeLuca et al. |
| 6,248,115 B1 | 6/2001 | Halk |
| 6,287,252 B1 | 9/2001 | Lugo |
| 6,290,707 B1 | 9/2001 | Street |
| 6,315,719 B1 | 11/2001 | Rode et al. |
| 6,379,237 B1 | 4/2002 | Gordon |
| 6,385,473 B1 | 5/2002 | Haines et al. |
| 6,389,308 B1 | 5/2002 | Shusterman |
| 6,416,471 B1 | 7/2002 | Kumar et al. |
| 6,434,410 B1 | 8/2002 | Cordero et al. |
| 6,441,747 B1 | 8/2002 | Khair et al. |
| 6,453,186 B1 | 9/2002 | Lovejoy et al. |
| 6,454,708 B1 | 9/2002 | Ferguson et al. |
| 6,456,871 B1 | 9/2002 | Hsu et al. |
| 6,456,872 B1 | 9/2002 | Faisandier |
| 6,464,815 B1 | 10/2002 | Beaudry |
| 6,493,898 B1 | 12/2002 | Woods et al. |
| 6,496,705 B1 | 12/2002 | Ng et al. |
| 6,510,339 B2 | 1/2003 | Kovtun et al. |
| 6,546,285 B1 | 4/2003 | Owen et al. |
| 6,564,090 B2 | 5/2003 | Taha et al. |
| 6,569,095 B2 | 5/2003 | Eggers |
| 6,577,893 B1 | 6/2003 | Besson et al. |
| 6,580,942 B1 | 6/2003 | Willshire |
| 6,585,707 B2 | 7/2003 | Cabiri et al. |
| 6,589,170 B1 | 7/2003 | Flach et al. |
| 6,589,187 B1 | 7/2003 | Dimberger et al. |
| 6,605,046 B1 | 8/2003 | Del Mar et al. |
| 6,615,083 B2 | 9/2003 | Kupper |
| 6,622,035 B1 | 9/2003 | Merilainen |
| 6,626,865 B1 | 9/2003 | Prisell |
| 6,656,125 B2 | 12/2003 | Misczynski et al. |
| 6,664,893 B1 | 12/2003 | Eveland et al. |
| 6,665,385 B2 | 12/2003 | Rogers et al. |
| 6,690,959 B2 | 2/2004 | Thompson |
| 6,694,177 B2 | 2/2004 | Eggers et al. |
| 6,701,184 B2 | 3/2004 | Henkin |
| 6,711,427 B1 | 3/2004 | Ketelhohn |
| 6,730,028 B2 | 5/2004 | Eppstein |
| D492,607 S | 7/2004 | Curkovic et al. |
| 6,773,396 B2 | 8/2004 | Flach et al. |
| 6,775,566 B2 | 8/2004 | Nissila |
| 6,801,137 B2 | 10/2004 | Eggers |
| 6,801,802 B2 | 10/2004 | Sitzman et al. |
| 6,871,089 B2 | 3/2005 | Korzinov et al. |
| 6,871,211 B2 | 3/2005 | Labounty et al. |
| 6,875,174 B2 | 4/2005 | Braun et al. |
| 6,881,191 B2 | 4/2005 | Oakley et al. |
| 6,893,396 B2 | 5/2005 | Schulze et al. |
| 6,897,788 B2 | 5/2005 | Khair et al. |
| 6,904,312 B2 | 6/2005 | Bardy |
| 6,925,324 B2 | 8/2005 | Shusterman |
| 6,940,403 B2 | 9/2005 | Kail |
| 6,954,163 B2 | 10/2005 | Toumazou et al. |
| 6,957,107 B2 | 10/2005 | Rogers et al. |
| 6,987,965 B2 | 1/2006 | Ng et al. |
| 7,002,468 B2 | 2/2006 | Eveland et al. |
| 7,020,508 B2 | 3/2006 | Stivoric et al. |
| 7,024,248 B2 | 4/2006 | Penner et al. |
| 7,031,770 B2 | 4/2006 | Collins et al. |
| 7,072,708 B1 | 7/2006 | Andresen et al. |
| 7,072,709 B2 | 7/2006 | Xue |
| 7,076,283 B2 | 7/2006 | Cho et al. |
| 7,076,287 B2 | 7/2006 | Rowlandson |
| 7,076,288 B2 | 7/2006 | Skinner |
| 7,076,289 B2 | 7/2006 | Sarkar et al. |
| 7,079,977 B2 | 7/2006 | Osorio et al. |
| 7,082,327 B2 | 7/2006 | Houben |
| 7,089,048 B2 | 8/2006 | Matsumura et al. |
| 7,099,715 B2 | 8/2006 | Korzinov et al. |
| 7,117,031 B2 | 10/2006 | Lohman et al. |
| 7,120,485 B2 | 10/2006 | Glass et al. |
| 7,130,396 B2 | 10/2006 | Rogers et al. |
| 7,161,484 B2 | 1/2007 | Tsoukalis |
| 7,171,166 B2 | 1/2007 | Ng et al. |
| 7,179,152 B1 | 2/2007 | Rhoades |
| 7,186,264 B2 | 3/2007 | Liddicoat et al. |
| 7,193,264 B2 | 3/2007 | Lande |
| 7,194,300 B2 | 3/2007 | Korzinov |
| 7,206,630 B1 | 4/2007 | Tarler |
| 7,212,850 B2 | 5/2007 | Prystowsky et al. |
| 7,222,054 B2 | 5/2007 | Geva |
| 7,242,318 B2 | 7/2007 | Harris |
| 7,266,361 B2 | 9/2007 | Burdett |
| 7,316,671 B2 | 1/2008 | Lastovich et al. |
| 7,349,947 B1 | 3/2008 | Slage et al. |
| D567,949 S | 4/2008 | Lash et al. |
| 7,354,423 B2 | 4/2008 | Zelickson et al. |
| 7,387,607 B2 | 6/2008 | Holt et al. |
| 7,444,177 B2 | 10/2008 | Nazeri |
| D584,414 S | 1/2009 | Lash et al. |
| 7,477,933 B2 | 1/2009 | Ueyama |
| 7,478,108 B2 | 1/2009 | Townsend et al. |
| 7,481,772 B2 | 1/2009 | Banet |
| 7,482,314 B2 | 1/2009 | Grimes et al. |
| 7,502,643 B2 | 3/2009 | Farringdon et al. |
| 7,539,533 B2 | 5/2009 | Tran |
| 7,542,878 B2 | 6/2009 | Nanikashvili |
| D600,351 S | 9/2009 | Phillips et al. |
| 7,587,237 B2 | 9/2009 | Korzinov et al. |
| 7,630,756 B2 | 12/2009 | Linker |
| 7,632,174 B2 | 12/2009 | Gringer et al. |
| D607,570 S | 1/2010 | Phillips et al. |
| 7,672,714 B2 | 3/2010 | Kuo et al. |
| 7,715,905 B2 | 5/2010 | Kurzweil et al. |
| D618,357 S | 6/2010 | Navies |
| 7,729,753 B2 | 6/2010 | Kremliovsky et al. |
| 7,733,224 B2 | 6/2010 | Tran |
| D621,048 S | 8/2010 | Severe et al. |
| 7,815,494 B2 | 10/2010 | Gringer et al. |
| 7,841,039 B1 | 11/2010 | Squire |
| 7,889,070 B2 | 2/2011 | Reeves et al. |
| 7,894,888 B2 | 2/2011 | Chan et al. |
| D634,431 S | 3/2011 | Severe et al. |
| 7,904,133 B2 | 3/2011 | Gehman et al. |
| 7,907,956 B2 | 3/2011 | Uhlik |
| 7,907,996 B2 | 3/2011 | Prystowsky et al. |
| 7,941,207 B2 | 5/2011 | Korzinov |
| D639,437 S | 6/2011 | Bishay et al. |
| 7,970,450 B2 | 6/2011 | Kroecker et al. |
| 7,979,111 B2 | 7/2011 | Acquista |
| 7,996,075 B2 | 8/2011 | Korzinov et al. |
| 7,996,187 B2 | 8/2011 | Nanikashvili et al. |
| 8,002,701 B2 | 8/2011 | John et al. |
| D645,968 S | 9/2011 | Kasabach et al. |
| D650,911 S | 12/2011 | Odeh |
| 8,077,042 B2 | 12/2011 | Peeters |
| 8,103,333 B2 | 1/2012 | Tran |
| 8,108,036 B2 | 1/2012 | Tran |
| 8,116,841 B2 | 2/2012 | Bly et al. |
| 8,150,502 B2 | 4/2012 | Kumar et al. |
| 8,156,945 B2 | 4/2012 | Hart |
| 8,160,682 B2 | 4/2012 | Kumar et al. |
| D659,836 S | 5/2012 | Bensch et al. |
| 8,170,639 B2 | 5/2012 | Hauge |
| 8,200,319 B2 | 6/2012 | Pu et al. |
| D663,432 S | 7/2012 | Nichols |
| 8,214,007 B2 | 7/2012 | Baker et al. |
| 8,244,335 B2 | 8/2012 | Kumar et al. |
| 8,249,686 B2 | 8/2012 | Libbus et al. |
| 8,261,754 B2 | 9/2012 | Pitstick |
| 8,265,907 B2 | 9/2012 | Nanikashvili et al. |
| RE43,767 E | 10/2012 | Eggers et al. |
| 8,280,749 B2 | 10/2012 | Hsieh et al. |
| 8,285,356 B2 | 10/2012 | Bly et al. |
| 8,290,129 B2 | 10/2012 | Rogers et al. |
| 8,290,574 B2 | 10/2012 | Field et al. |
| 8,301,219 B2 | 10/2012 | Chen et al. |
| 8,301,236 B2 | 10/2012 | Baumann et al. |
| 8,311,604 B2 | 11/2012 | Rowlandson et al. |
| 8,315,687 B2 | 11/2012 | Cross et al. |
| 8,315,695 B2 | 11/2012 | Sebelius et al. |
| 8,323,188 B2 | 12/2012 | Tran |

(56) References Cited

U.S. PATENT DOCUMENTS

| | | |
|---|---|---|
| 8,326,394 B2 | 12/2012 | Rowlandson et al. |
| 8,326,407 B2 | 12/2012 | Linker |
| 8,328,718 B2 | 12/2012 | Tran |
| D674,009 S | 1/2013 | Nichols |
| 8,343,116 B2 | 1/2013 | Ignon |
| 8,369,936 B2 | 2/2013 | Farringdon et al. |
| 8,374,688 B2 | 2/2013 | Libbus et al. |
| 8,386,009 B2 | 2/2013 | Lindberg et al. |
| 8,388,543 B2 | 3/2013 | Chon et al. |
| 8,406,843 B2 | 3/2013 | Tiegs et al. |
| 8,412,317 B2 | 4/2013 | Mazar |
| 8,417,326 B2 | 4/2013 | Chon et al. |
| 8,425,414 B2 | 4/2013 | Eveland |
| D682,437 S | 5/2013 | Olson et al. |
| 8,449,471 B2 | 5/2013 | Tran |
| 8,452,356 B2 | 5/2013 | Vestel et al. |
| 8,460,189 B2 | 6/2013 | Libbus et al. |
| 8,473,039 B2 | 6/2013 | Michelson et al. |
| 8,473,047 B2 | 6/2013 | Chakravarthy et al. |
| 8,478,418 B2 | 7/2013 | Fahey |
| 8,483,809 B2 | 7/2013 | Kim et al. |
| 8,500,636 B2 | 8/2013 | Tran |
| 8,515,529 B2 | 8/2013 | Pu et al. |
| 8,525,673 B2 | 9/2013 | Tran |
| 8,535,223 B2 | 9/2013 | Corroy et al. |
| 8,538,503 B2 | 9/2013 | Kumar et al. |
| 8,540,731 B2 | 9/2013 | Kay |
| 8,560,046 B2 | 10/2013 | Kumar et al. |
| 8,562,527 B2 | 10/2013 | Braun et al. |
| 8,571,645 B2 | 10/2013 | Wu et al. |
| 8,588,908 B2 | 11/2013 | Moorman et al. |
| 8,591,430 B2 | 11/2013 | Amurthur et al. |
| 8,591,599 B1 | 11/2013 | Kaliki |
| 8,594,763 B1 | 11/2013 | Bibian |
| 8,626,262 B2 | 1/2014 | McGusty et al. |
| 8,639,319 B2 | 1/2014 | Hugh et al. |
| 8,668,643 B2 | 3/2014 | Kinast |
| 8,684,900 B2 | 4/2014 | Tran |
| 8,684,925 B2 | 4/2014 | Amurthur et al. |
| 8,688,189 B2 | 4/2014 | Shennib |
| 8,688,190 B2 | 4/2014 | Libbus et al. |
| 8,688,202 B2 | 4/2014 | Brockway et al. |
| 8,718,742 B2 | 5/2014 | Beck et al. |
| 8,718,752 B2 | 5/2014 | Libbus et al. |
| 8,718,753 B2 | 5/2014 | Chon et al. |
| 8,731,632 B1 | 5/2014 | Sereboff et al. |
| 8,738,118 B2 | 5/2014 | Moon et al. |
| 8,744,561 B2 | 6/2014 | Fahey |
| 8,755,876 B2 | 6/2014 | Chon et al. |
| 8,782,308 B2 | 7/2014 | Vlach |
| 8,789,727 B2 | 7/2014 | Mortazavi |
| 8,790,257 B2 | 7/2014 | Libbus et al. |
| 8,795,174 B2 | 8/2014 | Manicka et al. |
| 8,818,481 B2 | 8/2014 | Bly et al. |
| 8,823,490 B2 | 9/2014 | Libbus et al. |
| 8,838,218 B2 | 9/2014 | Khair |
| 8,858,450 B2 | 10/2014 | Chon et al. |
| 8,874,185 B2 | 10/2014 | Sonnenborg |
| D719,267 S | 12/2014 | Vaccarella |
| 8,903,477 B2 | 12/2014 | Berkner |
| 8,903,484 B2 | 12/2014 | Mazar |
| 8,909,328 B2 | 12/2014 | Chon |
| 8,909,330 B2 | 12/2014 | McCombie et al. |
| 8,909,332 B2 | 12/2014 | Vitali et al. |
| 8,909,333 B2 | 12/2014 | Rossi |
| 8,909,832 B2 | 12/2014 | Vlach et al. |
| 8,926,509 B2 | 1/2015 | Magar et al. |
| 8,945,019 B2 | 2/2015 | Prystowsky et al. |
| 8,948,854 B2 | 2/2015 | Friedman et al. |
| 8,954,129 B1 | 2/2015 | Schlegel et al. |
| 8,956,293 B2 | 2/2015 | McCombie et al. |
| 8,968,195 B2 | 3/2015 | Tran |
| 8,972,000 B2 | 3/2015 | Manera |
| 8,979,755 B2 | 3/2015 | Szydlo-Moore et al. |
| 9,014,777 B2 | 4/2015 | Woo |
| 9,015,008 B2 | 4/2015 | Geva et al. |
| 9,017,255 B2 | 4/2015 | Raptis et al. |
| 9,017,256 B2 | 4/2015 | Gottesman |
| 9,021,161 B2 | 4/2015 | Vlach et al. |
| 9,021,165 B2 | 4/2015 | Vlach |
| 9,026,190 B2 | 5/2015 | Shenasa et al. |
| 9,037,223 B2 | 5/2015 | Oral et al. |
| 9,044,148 B2 | 6/2015 | Michelson et al. |
| 9,084,548 B2 | 7/2015 | Bouguerra |
| 9,095,274 B2 | 8/2015 | Fein et al. |
| 9,101,264 B2 | 8/2015 | Acquista |
| 9,138,144 B2 | 9/2015 | Geva |
| 9,149,228 B2 | 10/2015 | Kinast |
| 9,173,670 B2 | 11/2015 | Sepulveda et al. |
| 9,179,851 B2 | 11/2015 | Baumann et al. |
| D744,659 S | 12/2015 | Bishay et al. |
| 9,211,076 B2 | 12/2015 | Kim |
| 9,226,679 B2 | 1/2016 | Balda |
| 9,241,649 B2 | 1/2016 | Kumar et al. |
| 9,241,650 B2 | 1/2016 | Amirim |
| 9,277,864 B2 | 3/2016 | Yang et al. |
| 9,282,894 B2 | 3/2016 | Banet et al. |
| 9,307,921 B2 | 4/2016 | Friedman et al. |
| 9,345,414 B1 | 5/2016 | Bardy et al. |
| 9,355,215 B2 | 5/2016 | Vlach |
| D759,653 S | 6/2016 | Toth et al. |
| 9,357,939 B1 | 6/2016 | Nosrati |
| 9,364,150 B2 | 6/2016 | Sebelius et al. |
| 9,364,155 B2 | 6/2016 | Bardy et al. |
| 9,398,853 B2 | 7/2016 | Nanikashvili |
| 9,408,545 B2 | 8/2016 | Felix et al. |
| 9,408,551 B2 | 8/2016 | Bardy et al. |
| 9,408,576 B2 | 8/2016 | Chon et al. |
| 9,414,753 B2 | 8/2016 | Chon et al. |
| 9,414,786 B1 | 8/2016 | Brockway et al. |
| D766,447 S | 9/2016 | Bishay et al. |
| 9,433,367 B2 | 9/2016 | Felix et al. |
| 9,433,380 B1 | 9/2016 | Bishay et al. |
| 9,439,566 B2 | 9/2016 | Arne et al. |
| 9,439,599 B2 | 9/2016 | Thompson et al. |
| 9,445,719 B2 | 9/2016 | Libbus et al. |
| 9,451,890 B2 | 9/2016 | Gitlin et al. |
| 9,451,975 B2 | 9/2016 | Sepulveda et al. |
| 9,474,445 B2 | 10/2016 | Eveland |
| 9,474,461 B2 | 10/2016 | Fisher et al. |
| 9,478,998 B1 | 10/2016 | Lapetina et al. |
| D773,056 S | 11/2016 | Vlach |
| 9,492,084 B2 | 11/2016 | Behar et al. |
| 9,504,423 B1 | 11/2016 | Bardy et al. |
| D775,361 S | 12/2016 | Vosch et al. |
| 9,510,764 B2 | 12/2016 | Li et al. |
| 9,510,768 B2 | 12/2016 | Rossi |
| 9,526,433 B2 | 12/2016 | Lapetina et al. |
| 9,545,204 B2 | 1/2017 | Bishay et al. |
| 9,545,228 B2 | 1/2017 | Bardy et al. |
| 9,554,715 B2 | 1/2017 | Bardy et al. |
| 9,579,020 B2 | 2/2017 | Libbus et al. |
| D780,914 S | 3/2017 | Kyvik et al. |
| 9,585,584 B2 | 3/2017 | Marek et al. |
| 9,597,004 B2 | 3/2017 | Hughes et al. |
| 9,615,763 B2 | 4/2017 | Felix et al. |
| 9,615,793 B2 | 4/2017 | Solosko et al. |
| 9,619,660 B1 | 4/2017 | Felix et al. |
| 9,642,537 B2 | 5/2017 | Felix et al. |
| 9,655,518 B2 | 5/2017 | Lin |
| 9,655,537 B2 | 5/2017 | Bardy et al. |
| 9,655,538 B2 | 5/2017 | Felix |
| 9,662,030 B2 | 5/2017 | Thng et al. |
| 9,675,264 B2 | 6/2017 | Acquista et al. |
| 9,700,227 B2 | 7/2017 | Bishay et al. |
| 9,706,938 B2 | 7/2017 | Chakravarthy et al. |
| 9,706,956 B2 | 7/2017 | Brockway et al. |
| 9,713,428 B2 | 7/2017 | Chon et al. |
| D793,566 S | 8/2017 | Bishay et al. |
| D794,812 S | 8/2017 | Matsushita |
| 9,717,432 B2 | 8/2017 | Bardy et al. |
| 9,717,433 B2 | 8/2017 | Felix et al. |
| 9,730,593 B2 | 8/2017 | Bardy et al. |
| 9,730,604 B2 | 8/2017 | Li et al. |

(56) References Cited

U.S. PATENT DOCUMENTS

| | | |
|---|---|---|
| 9,730,641 B2 | 8/2017 | Felix et al. |
| 9,736,625 B1 | 8/2017 | Landgraf et al. |
| 9,737,211 B2 | 8/2017 | Bardy et al. |
| 9,737,224 B2 | 8/2017 | Bardy et al. |
| D797,301 S | 9/2017 | Chen |
| D797,943 S | 9/2017 | Long |
| D798,170 S | 9/2017 | Toth et al. |
| D798,294 S | 9/2017 | Toth et al. |
| 9,775,534 B2 | 10/2017 | Korzinov et al. |
| 9,775,536 B2 | 10/2017 | Felix et al. |
| 9,782,095 B2 | 10/2017 | Ylostalo et al. |
| 9,782,132 B2 | 10/2017 | Golda et al. |
| 9,788,722 B2 | 10/2017 | Bardy et al. |
| 9,801,562 B1 | 10/2017 | Host-Madsen |
| 9,820,665 B2 | 11/2017 | Felix et al. |
| 9,839,363 B2 | 12/2017 | Albert |
| D810,308 S | 2/2018 | Lind et al. |
| D811,610 S | 2/2018 | Abel et al. |
| D811,611 S | 2/2018 | Lind et al. |
| D811,615 S | 2/2018 | Lind et al. |
| 9,888,866 B2 | 2/2018 | Chon et al. |
| 9,907,478 B2 | 3/2018 | Friedman et al. |
| 9,936,875 B2 | 4/2018 | Bardy et al. |
| 9,955,885 B2 | 5/2018 | Felix et al. |
| 9,955,887 B2 | 5/2018 | Hughes et al. |
| 9,955,888 B2 | 5/2018 | Felix et al. |
| 9,955,911 B2 | 5/2018 | Bardy et al. |
| 9,968,274 B2 | 5/2018 | Korzinov et al. |
| 9,986,921 B2 | 6/2018 | Chon et al. |
| 10,004,415 B2 | 6/2018 | Bishay et al. |
| D823,466 S | 7/2018 | Marogil |
| D824,526 S | 7/2018 | Ramjit et al. |
| 10,045,709 B2 | 8/2018 | Bardy et al. |
| 10,052,022 B2 | 8/2018 | Bardy et al. |
| 10,076,257 B2 | 9/2018 | Lin et al. |
| 10,095,841 B2 | 10/2018 | Dettinger et al. |
| 10,098,559 B2 | 10/2018 | Hughes et al. |
| 10,111,601 B2 | 10/2018 | Bishay et al. |
| 10,123,703 B2 | 11/2018 | Bardy et al. |
| 10,154,793 B2 | 12/2018 | Felix et al. |
| 10,165,946 B2 | 1/2019 | Bardy et al. |
| 10,172,534 B2 | 1/2019 | Felix et al. |
| 10,176,575 B2 | 1/2019 | Isgum et al. |
| 10,251,575 B2 | 4/2019 | Bardy et al. |
| 10,251,576 B2 | 4/2019 | Bardy et al. |
| 10,264,992 B2 | 4/2019 | Felix et al. |
| 10,265,015 B2 | 4/2019 | Bardy et al. |
| 10,270,898 B2 | 4/2019 | Soli et al. |
| 10,271,754 B2 | 4/2019 | Bahney et al. |
| 10,271,755 B2 | 4/2019 | Felix et al. |
| 10,271,756 B2 | 4/2019 | Felix et al. |
| 10,278,603 B2 | 5/2019 | Felix et al. |
| 10,278,606 B2 | 5/2019 | Bishay et al. |
| 10,278,607 B2 | 5/2019 | Prystowsky et al. |
| 10,299,691 B2 | 5/2019 | Hughes et al. |
| 10,321,823 B2 | 6/2019 | Chakravarthy et al. |
| 10,327,657 B2 | 6/2019 | Spencer et al. |
| D852,965 S | 7/2019 | Bahney et al. |
| D854,167 S | 7/2019 | Bahney et al. |
| 10,362,467 B2 | 7/2019 | Landgraf et al. |
| 10,368,808 B2 | 8/2019 | Lee et al. |
| 10,376,172 B2 | 8/2019 | Kuppuraj et al. |
| 10,390,700 B2 | 8/2019 | Bardy et al. |
| 10,398,344 B2 | 9/2019 | Felix et al. |
| 10,405,799 B2 | 9/2019 | Kumar et al. |
| 10,413,205 B2 | 9/2019 | Bardy et al. |
| 10,426,634 B1 | 10/2019 | Al-Jazaeri et al. |
| 10,433,743 B1 | 10/2019 | Felix et al. |
| 10,433,748 B2 | 10/2019 | Bishay et al. |
| 10,433,751 B2 | 10/2019 | Bardy et al. |
| 10,441,184 B2 | 10/2019 | Baumann et al. |
| 10,463,269 B2 | 11/2019 | Boleyn et al. |
| 10,478,083 B2 | 11/2019 | Felix et al. |
| 10,499,812 B2 | 12/2019 | Bardy et al. |
| 10,517,500 B2 | 12/2019 | Kumar et al. |
| 10,555,683 B2 | 2/2020 | Bahney et al. |
| 10,561,326 B2 | 2/2020 | Felix et al. |
| 10,561,328 B2 | 2/2020 | Bishay |
| 10,568,533 B2 | 2/2020 | Soli et al. |
| 10,588,527 B2 | 3/2020 | McNamara et al. |
| 10,595,371 B2 | 3/2020 | Gopalakrishnan et al. |
| 10,602,942 B2 | 3/2020 | Shakur et al. |
| 10,602,977 B2 | 3/2020 | Bardy et al. |
| 10,624,551 B2 | 4/2020 | Bardy et al. |
| 10,660,520 B2 | 5/2020 | Lin |
| 10,667,712 B2 | 6/2020 | Park et al. |
| 10,729,361 B2 | 8/2020 | Hoppe et al. |
| 10,758,139 B2 | 9/2020 | Rapin et al. |
| 10,772,521 B2 | 9/2020 | Korzinov et al. |
| 10,779,744 B2 | 9/2020 | Rapin et al. |
| 10,813,565 B2 | 10/2020 | Park et al. |
| 10,827,938 B2 | 11/2020 | Fontanarava et al. |
| 10,866,619 B1 | 12/2020 | Bushnell et al. |
| 10,869,610 B2 | 12/2020 | Lu et al. |
| 10,987,018 B2 | 4/2021 | Aga et al. |
| 11,004,198 B2 | 5/2021 | Isgum et al. |
| 11,017,887 B2 | 5/2021 | Finkelmeier et al. |
| 11,026,632 B2 | 6/2021 | Narasimhan et al. |
| 11,051,738 B2 | 7/2021 | Bahney et al. |
| 11,051,743 B2 | 7/2021 | Felix et al. |
| 11,062,804 B2 | 7/2021 | Selvaraj et al. |
| 11,083,371 B1 | 8/2021 | Szabados et al. |
| 11,141,091 B2 | 10/2021 | Uday et al. |
| 11,172,882 B2 | 11/2021 | Upadhya et al. |
| 11,246,523 B1 | 2/2022 | Abercrombie, II et al. |
| 11,246,524 B2 | 2/2022 | Szabados et al. |
| 11,253,185 B2 | 2/2022 | Szabados et al. |
| 11,253,186 B2 | 2/2022 | Szabados et al. |
| 11,276,491 B2 | 3/2022 | Petterson et al. |
| 11,289,197 B1 | 3/2022 | Park et al. |
| 11,324,420 B2 | 5/2022 | Selvaraj et al. |
| 11,324,441 B2 | 5/2022 | Bardy et al. |
| 11,331,034 B2 | 5/2022 | Rapin et al. |
| 11,337,632 B2 | 5/2022 | Abercrombie, II et al. |
| 11,350,864 B2 | 6/2022 | Abercrombie, II et al. |
| 11,350,865 B2 | 6/2022 | Abercrombie, II et al. |
| 11,375,941 B2 | 7/2022 | Szabados et al. |
| 11,382,555 B2 | 7/2022 | Szabados et al. |
| 11,399,760 B2 | 8/2022 | Abercrombie, II et al. |
| 11,445,967 B2 | 9/2022 | Felix et al. |
| 11,497,432 B2 | 11/2022 | Szabados et al. |
| 11,504,041 B2 | 11/2022 | Abercrombie, II et al. |
| 11,589,792 B1 | 2/2023 | Abercrombie, II et al. |
| 11,605,458 B2 | 3/2023 | Park et al. |
| 11,627,902 B2 | 4/2023 | Bahney et al. |
| 11,660,037 B2 | 5/2023 | Felix et al. |
| D988,518 S | 6/2023 | Levy et al. |
| 11,678,832 B2 | 6/2023 | Boleyn et al. |
| 11,751,789 B2 | 9/2023 | Abercrombie, II et al. |
| 11,756,684 B2 | 9/2023 | Park et al. |
| 11,806,150 B2 | 11/2023 | Abercrombie, II et al. |
| D1,012,295 S | 1/2024 | Peremen et al. |
| 11,925,469 B2 | 3/2024 | Szabados et al. |
| 12,133,731 B2 | 11/2024 | Abercrombie, II et al. |
| 12,133,734 B2 | 11/2024 | Kumar et al. |
| 12,213,791 B2 | 2/2025 | Abercrombie, II et al. |
| 12,245,859 B2 | 3/2025 | Bahney et al. |
| 12,245,860 B2 | 3/2025 | Bahney et al. |
| 12,274,554 B2 | 4/2025 | Kumar et al. |
| 2001/0056262 A1 | 12/2001 | Cabiri et al. |
| 2002/0007126 A1 | 1/2002 | Nissila |
| 2002/0026112 A1 | 2/2002 | Nissila et al. |
| 2002/0067256 A1 | 6/2002 | Kail |
| 2002/0082491 A1 | 6/2002 | Nissila |
| 2002/0087167 A1 | 7/2002 | Winitsky |
| 2002/0180605 A1 | 12/2002 | Ozguz et al. |
| 2003/0069510 A1 | 4/2003 | Semler |
| 2003/0083559 A1 | 5/2003 | Thompson |
| 2003/0125786 A1 | 7/2003 | Gliner |
| 2003/0149349 A1 | 8/2003 | Jensen |
| 2003/0176795 A1 | 9/2003 | Harris et al. |
| 2003/0195408 A1 | 10/2003 | Hastings |
| 2003/0199811 A1 | 10/2003 | Sage, Jr. et al. |
| 2003/0212319 A1 | 11/2003 | Magill |

(56) References Cited

U.S. PATENT DOCUMENTS

| | | |
|---|---|---|
| 2004/0032957 A1 | 2/2004 | Mansy et al. |
| 2004/0068195 A1 | 4/2004 | Massicotte et al. |
| 2004/0077954 A1 | 4/2004 | Oakley et al. |
| 2004/0082843 A1 | 4/2004 | Menon |
| 2004/0187297 A1 | 9/2004 | Su |
| 2004/0199063 A1 | 10/2004 | O'Neil |
| 2004/0215091 A1 | 10/2004 | Lohman et al. |
| 2004/0236202 A1 | 11/2004 | Burton |
| 2004/0238819 A1 | 12/2004 | Maghribi et al. |
| 2004/0254587 A1 | 12/2004 | Park |
| 2004/0260189 A1 | 12/2004 | Eggers et al. |
| 2005/0096513 A1 | 5/2005 | Ozguz et al. |
| 2005/0101875 A1 | 5/2005 | Semler et al. |
| 2005/0118246 A1 | 6/2005 | Wong et al. |
| 2005/0119580 A1 | 6/2005 | Eveland |
| 2005/0165323 A1 | 7/2005 | Montgomery et al. |
| 2005/0204636 A1 | 9/2005 | Azar et al. |
| 2005/0277841 A1 | 12/2005 | Shennib |
| 2005/0280531 A1 | 12/2005 | Fadem et al. |
| 2006/0030781 A1 | 2/2006 | Shennib |
| 2006/0030782 A1 | 2/2006 | Shennib |
| 2006/0047215 A1 | 3/2006 | Newman et al. |
| 2006/0084883 A1 | 4/2006 | Linker |
| 2006/0142648 A1 | 6/2006 | Banet et al. |
| 2006/0142654 A1 | 6/2006 | Rytky |
| 2006/0149156 A1 | 7/2006 | Cochran et al. |
| 2006/0155173 A1 | 7/2006 | Anttila et al. |
| 2006/0155183 A1 | 7/2006 | Kroecker et al. |
| 2006/0155199 A1 | 7/2006 | Logier et al. |
| 2006/0155200 A1 | 7/2006 | Ng et al. |
| 2006/0161064 A1 | 7/2006 | Watrous et al. |
| 2006/0161065 A1 | 7/2006 | Elion |
| 2006/0161066 A1 | 7/2006 | Elion |
| 2006/0161067 A1 | 7/2006 | Elion |
| 2006/0161068 A1 | 7/2006 | Hastings et al. |
| 2006/0167353 A1 | 7/2006 | Nazeri |
| 2006/0224072 A1 | 10/2006 | Shennib |
| 2006/0264767 A1 | 11/2006 | Shennib |
| 2007/0003695 A1 | 1/2007 | Tregub et al. |
| 2007/0010729 A1 | 1/2007 | Virtanen |
| 2007/0027388 A1 | 2/2007 | Chou |
| 2007/0088419 A1 | 4/2007 | Florina et al. |
| 2007/0156054 A1 | 7/2007 | Korzinov et al. |
| 2007/0208266 A1 | 9/2007 | Hadley |
| 2007/0225611 A1 | 9/2007 | Kumar et al. |
| 2007/0249946 A1 | 10/2007 | Kumar et al. |
| 2007/0255153 A1 | 11/2007 | Kumar et al. |
| 2007/0270678 A1 | 11/2007 | Fadem et al. |
| 2007/0285868 A1 | 12/2007 | Lindberg et al. |
| 2007/0293776 A1 | 12/2007 | Korzinov et al. |
| 2007/0299325 A1 | 12/2007 | Farrell |
| 2008/0039730 A1 | 2/2008 | Pu et al. |
| 2008/0091089 A1 | 4/2008 | Guillory et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0167567 A1 | 7/2008 | Bashour et al. |
| 2008/0214901 A1 | 9/2008 | Gehman et al. |
| 2008/0275327 A1 | 11/2008 | Faarbaek et al. |
| 2008/0281215 A1 | 11/2008 | Alhussiny |
| 2008/0288026 A1 | 11/2008 | Cross et al. |
| 2008/0309287 A1 | 12/2008 | Reed |
| 2009/0048556 A1 | 2/2009 | Durand |
| 2009/0062670 A1 | 3/2009 | Sterling et al. |
| 2009/0062671 A1 | 3/2009 | Brockway |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0182204 A1 | 7/2009 | Semler et al. |
| 2009/0253975 A1 | 10/2009 | Tiegs |
| 2009/0283300 A1 | 11/2009 | Grunthaner |
| 2009/0292193 A1 | 11/2009 | Wijesiriwardana |
| 2009/0292194 A1 | 11/2009 | Libbus et al. |
| 2009/0306485 A1 | 12/2009 | Bell |
| 2010/0001541 A1 | 1/2010 | Sugiyama |
| 2010/0022864 A1 | 1/2010 | Cordero |
| 2010/0042113 A1 | 2/2010 | Mah |
| 2010/0049006 A1 | 2/2010 | Magar et al. |
| 2010/0051039 A1 | 3/2010 | Ferrara |
| 2010/0056881 A1 | 3/2010 | Libbus et al. |
| 2010/0057056 A1 | 3/2010 | Gurtner |
| 2010/0076533 A1 | 3/2010 | Dar et al. |
| 2010/0081913 A1 | 4/2010 | Cross et al. |
| 2010/0145359 A1 | 6/2010 | Keller |
| 2010/0191310 A1 | 7/2010 | Bly |
| 2010/0234716 A1 | 9/2010 | Engel |
| 2010/0249625 A1 | 9/2010 | Lin |
| 2010/0268103 A1 | 10/2010 | McNamara et al. |
| 2010/0312131 A1 | 12/2010 | Naware et al. |
| 2010/0331711 A1 | 12/2010 | Krauss et al. |
| 2011/0021937 A1 | 1/2011 | Hugh et al. |
| 2011/0087083 A1 | 4/2011 | Poeze et al. |
| 2011/0098583 A1 | 4/2011 | Pandia et al. |
| 2011/0119212 A1 | 5/2011 | De Bruin et al. |
| 2011/0144470 A1 | 6/2011 | Mazar et al. |
| 2011/0160601 A1 | 6/2011 | Wang et al. |
| 2011/0166468 A1 | 7/2011 | Prystowsky et al. |
| 2011/0190650 A1 | 8/2011 | McNair |
| 2011/0218415 A1 | 9/2011 | Chen |
| 2011/0237922 A1 | 9/2011 | Parker, III et al. |
| 2011/0237924 A1 | 9/2011 | McGusty et al. |
| 2011/0251504 A1 | 10/2011 | Tereshchenko et al. |
| 2011/0279963 A1 | 11/2011 | Kumar et al. |
| 2011/0306862 A1 | 12/2011 | Hayes-Gill |
| 2012/0029307 A1 | 2/2012 | Paquet et al. |
| 2012/0071730 A1 | 3/2012 | Romero |
| 2012/0071731 A1 | 3/2012 | Gottesman |
| 2012/0071743 A1 | 3/2012 | Todorov et al. |
| 2012/0083670 A1 | 4/2012 | Rotondo et al. |
| 2012/0088999 A1 | 4/2012 | Bishay et al. |
| 2012/0101396 A1 | 4/2012 | Solosko et al. |
| 2012/0108917 A1 | 5/2012 | Libbus et al. |
| 2012/0108920 A1 | 5/2012 | Bly et al. |
| 2012/0110226 A1 | 5/2012 | Vlach et al. |
| 2012/0110228 A1 | 5/2012 | Vlach et al. |
| 2012/0123232 A1 | 5/2012 | Najarian et al. |
| 2012/0133162 A1 | 5/2012 | Sgobero |
| 2012/0172676 A1 | 7/2012 | Penders et al. |
| 2012/0197150 A1 | 8/2012 | Cao et al. |
| 2012/0209102 A1 | 8/2012 | Ylotalo et al. |
| 2012/0209126 A1 | 8/2012 | Amos et al. |
| 2012/0215123 A1 | 8/2012 | Kumar et al. |
| 2012/0220835 A1 | 8/2012 | Chung |
| 2012/0259233 A1 | 10/2012 | Chan et al. |
| 2012/0271141 A1 | 10/2012 | Davies |
| 2012/0310070 A1 | 12/2012 | Kumar et al. |
| 2012/0316532 A1 | 12/2012 | McCormick |
| 2012/0323257 A1 | 12/2012 | Sutton |
| 2012/0330126 A1 | 12/2012 | Hoppe et al. |
| 2013/0023816 A1 | 1/2013 | Bachinski et al. |
| 2013/0041273 A1 | 2/2013 | Houben et al. |
| 2013/0046151 A1 | 2/2013 | Bsoul et al. |
| 2013/0085347 A1 | 4/2013 | Manicka et al. |
| 2013/0096395 A1 | 4/2013 | Katra et al. |
| 2013/0116533 A1 | 5/2013 | Lian et al. |
| 2013/0116585 A1 | 5/2013 | Bouguerra |
| 2013/0144146 A1 | 6/2013 | Linker |
| 2013/0150698 A1 | 6/2013 | Hsu et al. |
| 2013/0158494 A1 | 6/2013 | Ong |
| 2013/0172763 A1 | 7/2013 | Wheeler |
| 2013/0184662 A1 | 7/2013 | Aali et al. |
| 2013/0191035 A1 | 7/2013 | Chon et al. |

(56) References Cited

U.S. PATENT DOCUMENTS

| | | |
|---|---|---|
| 2013/0225938 A1 | 8/2013 | Vlach |
| 2013/0225967 A1 | 8/2013 | Esposito |
| 2013/0226018 A1 | 8/2013 | Kumar et al. |
| 2013/0245415 A1 | 9/2013 | Kumar et al. |
| 2013/0245472 A1 | 9/2013 | Eveland |
| 2013/0253285 A1 | 9/2013 | Bly et al. |
| 2013/0274584 A1 | 10/2013 | Finlay et al. |
| 2013/0296680 A1 | 11/2013 | Linker |
| 2013/0300575 A1 | 11/2013 | Kurzweil et al. |
| 2013/0324868 A1 | 12/2013 | Kaib et al. |
| 2013/0331663 A1 | 12/2013 | Albert et al. |
| 2013/0331665 A1 | 12/2013 | Bly et al. |
| 2013/0338448 A1 | 12/2013 | Libbus et al. |
| 2014/0012154 A1 | 1/2014 | Mazar |
| 2014/0058280 A1 | 2/2014 | Chefles et al. |
| 2014/0088394 A1 | 3/2014 | Sunderland |
| 2014/0094676 A1 | 4/2014 | Gani et al. |
| 2014/0094709 A1 | 4/2014 | Korzinov et al. |
| 2014/0100432 A1 | 4/2014 | Golda et al. |
| 2014/0116825 A1 | 5/2014 | Lindeman |
| 2014/0171751 A1 | 6/2014 | Sankman et al. |
| 2014/0206976 A1 | 7/2014 | Thompson et al. |
| 2014/0206977 A1 | 7/2014 | Bahney et al. |
| 2014/0243621 A1 | 8/2014 | Weng et al. |
| 2014/0275827 A1 | 9/2014 | Gill et al. |
| 2014/0275840 A1 | 9/2014 | Osorio |
| 2014/0275928 A1 | 9/2014 | Acquista et al. |
| 2014/0303647 A1 | 10/2014 | Sepulveda et al. |
| 2014/0330136 A1 | 11/2014 | Manicka et al. |
| 2015/0005854 A1 | 1/2015 | Said |
| 2015/0022372 A1 | 1/2015 | Vosch |
| 2015/0057512 A1 | 2/2015 | Kapoor |
| 2015/0073252 A1 | 3/2015 | Mazar |
| 2015/0081959 A1 | 3/2015 | Vlach et al. |
| 2015/0082623 A1 | 3/2015 | Felix et al. |
| 2015/0087921 A1 | 3/2015 | Felix et al. |
| 2015/0087922 A1 | 3/2015 | Bardy et al. |
| 2015/0087923 A1 | 3/2015 | Bardy et al. |
| 2015/0087933 A1 | 3/2015 | Gibson et al. |
| 2015/0087948 A1 | 3/2015 | Bishay et al. |
| 2015/0087949 A1 | 3/2015 | Felix et al. |
| 2015/0087950 A1 | 3/2015 | Felix et al. |
| 2015/0087951 A1 | 3/2015 | Felix et al. |
| 2015/0088007 A1 | 3/2015 | Bardy et al. |
| 2015/0088020 A1 | 3/2015 | Dreisbach et al. |
| 2015/0094556 A1 | 4/2015 | Geva et al. |
| 2015/0148637 A1 | 5/2015 | Golda et al. |
| 2015/0157273 A1 | 6/2015 | An et al. |
| 2015/0173671 A1 | 6/2015 | Paalasmaa et al. |
| 2015/0193595 A1 | 7/2015 | McNamara et al. |
| 2015/0223711 A1 | 8/2015 | Raeder et al. |
| 2015/0238107 A1 | 8/2015 | Acquista et al. |
| 2015/0289814 A1 | 10/2015 | Magar et al. |
| 2015/0297134 A1 | 10/2015 | Albert et al. |
| 2015/0327781 A1 | 11/2015 | Hernandez-Silverira et al. |
| 2015/0351689 A1 | 12/2015 | Adams |
| 2015/0351799 A1 | 12/2015 | Sepulveda et al. |
| 2015/0374244 A1 | 12/2015 | Yoo et al. |
| 2016/0022161 A1 | 1/2016 | Khair |
| 2016/0029906 A1 | 2/2016 | Tompkins et al. |
| 2016/0066808 A1 | 3/2016 | Hijazi |
| 2016/0085927 A1 | 3/2016 | Dettinger et al. |
| 2016/0085937 A1 | 3/2016 | Dettinger et al. |
| 2016/0086297 A1 | 3/2016 | Dettinger et al. |
| 2016/0098536 A1 | 4/2016 | Dettinger et al. |
| 2016/0098537 A1 | 4/2016 | Dettinger et al. |
| 2016/0113520 A1 | 4/2016 | Manera |
| 2016/0120433 A1 | 5/2016 | Hughes et al. |
| 2016/0120434 A1 | 5/2016 | Park et al. |
| 2016/0128597 A1 | 5/2016 | Lin et al. |
| 2016/0135746 A1 | 5/2016 | Kumar et al. |
| 2016/0149292 A1 | 5/2016 | Ganton |
| 2016/0157744 A1 | 6/2016 | Wu et al. |
| 2016/0166155 A1 | 6/2016 | Banet et al. |
| 2016/0192852 A1 | 7/2016 | Bozza et al. |
| 2016/0192855 A1 | 7/2016 | Geva et al. |
| 2016/0192856 A1 | 7/2016 | Lee |
| 2016/0198972 A1 | 7/2016 | Lee et al. |
| 2016/0232807 A1 | 8/2016 | Ghaffari et al. |
| 2016/0262619 A1 | 9/2016 | Marcus et al. |
| 2016/0278658 A1 | 9/2016 | Bardy et al. |
| 2016/0287177 A1 | 10/2016 | Huppert et al. |
| 2016/0287207 A1 | 10/2016 | Xue |
| 2016/0296132 A1 | 10/2016 | Bojovic et al. |
| 2016/0302725 A1 | 10/2016 | Schultz et al. |
| 2016/0302726 A1 | 10/2016 | Chang |
| 2016/0317048 A1 | 11/2016 | Chan et al. |
| 2016/0317057 A1 | 11/2016 | Li et al. |
| 2016/0359150 A1 | 12/2016 | de Francisco Martin et al. |
| 2016/0361015 A1 | 12/2016 | Wang et al. |
| 2016/0367164 A1 | 12/2016 | Felix et al. |
| 2016/0374583 A1 | 12/2016 | Cerruti et al. |
| 2017/0042447 A1 | 2/2017 | Rossi |
| 2017/0055896 A1 | 3/2017 | Al-Ali et al. |
| 2017/0056682 A1 | 3/2017 | Kumar |
| 2017/0065823 A1 | 3/2017 | Kaib et al. |
| 2017/0076641 A1 | 3/2017 | Senanayake |
| 2017/0188872 A1 | 7/2017 | Hughes et al. |
| 2017/0188971 A1 | 7/2017 | Hughes et al. |
| 2018/0049698 A1 | 2/2018 | Berg |
| 2018/0049716 A1 | 2/2018 | Rajagopal et al. |
| 2018/0064388 A1 | 3/2018 | Heneghan et al. |
| 2018/0110266 A1 | 4/2018 | Lee et al. |
| 2018/0125387 A1 | 5/2018 | Hadley et al. |
| 2018/0144241 A1 | 5/2018 | Liu et al. |
| 2018/0146875 A1 | 5/2018 | Friedman et al. |
| 2018/0161211 A1 | 6/2018 | Beckey |
| 2018/0242876 A1 | 8/2018 | Hughes et al. |
| 2018/0257346 A1 | 9/2018 | Austin |
| 2018/0260706 A1 | 9/2018 | Galloway et al. |
| 2018/0289274 A1 | 10/2018 | Bahney et al. |
| 2018/0374576 A1 | 12/2018 | Dettinger et al. |
| 2019/0015008 A1 | 1/2019 | Alizadeh et al. |
| 2019/0021671 A1 | 1/2019 | Kumar et al. |
| 2019/0038148 A1 | 2/2019 | Valys |
| 2019/0046066 A1 | 2/2019 | Hughes et al. |
| 2019/0069788 A1 | 3/2019 | Coleman et al. |
| 2019/0090769 A1 | 3/2019 | Boleyn et al. |
| 2019/0097339 A1 | 3/2019 | Lim et al. |
| 2019/0098758 A1 | 3/2019 | Hassemer et al. |
| 2019/0099132 A1 | 4/2019 | Mulinti et al. |
| 2019/0133468 A1 | 5/2019 | Aliamiri et al. |
| 2019/0167143 A1 | 6/2019 | Li et al. |
| 2019/0209022 A1 | 7/2019 | Sobol |
| 2019/0246928 A1 | 8/2019 | Bahney et al. |
| 2019/0274574 A1 | 9/2019 | Hughes et al. |
| 2019/0282178 A1 | 9/2019 | Volosin et al. |
| 2019/0290147 A1 | 9/2019 | Persen et al. |
| 2019/0298201 A1 | 10/2019 | Persen et al. |
| 2019/0298209 A1 | 10/2019 | Persen et al. |
| 2019/0298272 A1 | 10/2019 | Persen |
| 2019/0374163 A1 | 12/2019 | Faabaek et al. |
| 2019/0378617 A1 | 12/2019 | Charles et al. |
| 2020/0060563 A1 | 2/2020 | Boleyn |
| 2020/0093388 A1 | 3/2020 | Bouguerra et al. |
| 2020/0100693 A1 | 4/2020 | Velo |
| 2020/0101278 A1 | 4/2020 | Freeman et al. |
| 2020/0108260 A1 | 4/2020 | Haddad et al. |
| 2020/0121209 A1 | 4/2020 | Kumar et al. |
| 2020/0170529 A1 | 6/2020 | Bahney et al. |
| 2020/0178825 A1 | 6/2020 | Lu |
| 2020/0178828 A1 | 6/2020 | Bahney et al. |
| 2020/0193597 A1 | 6/2020 | Fan et al. |
| 2020/0196897 A1 | 6/2020 | Biswas et al. |
| 2020/0214563 A1 | 7/2020 | Lin |
| 2020/0214584 A1 | 7/2020 | McNamara et al. |
| 2020/0237309 A1 | 7/2020 | Golda et al. |
| 2020/0289014 A1 | 9/2020 | Park et al. |
| 2020/0337608 A1 | 10/2020 | Garai et al. |
| 2020/0352489 A1 | 11/2020 | Hoppe et al. |
| 2020/0367779 A1 | 11/2020 | Korzinov et al. |
| 2020/0397313 A1 | 12/2020 | Attia et al. |
| 2021/0038102 A1 | 2/2021 | Boleyn et al. |
| 2021/0059612 A1 | 3/2021 | Krebs et al. |

(56) References Cited

U.S. PATENT DOCUMENTS

| | | | |
|---|---|---|---|
| 2021/0085215 | A1 | 3/2021 | Auerbach et al. |
| 2021/0085255 | A1 | 3/2021 | Vule et al. |
| 2021/0125722 | A1 | 4/2021 | Sherkat et al. |
| 2021/0153761 | A1 | 5/2021 | Jung et al. |
| 2021/0217519 | A1 | 7/2021 | Park et al. |
| 2021/0244279 | A1 | 8/2021 | Szabados et al. |
| 2021/0269046 | A1 | 9/2021 | Hashimoto et al. |
| 2021/0298688 | A1 | 9/2021 | Banerjee et al. |
| 2021/0304855 | A1 | 9/2021 | Ansari et al. |
| 2021/0315470 | A1 | 10/2021 | Wu et al. |
| 2021/0315504 | A1 | 10/2021 | Kumar et al. |
| 2021/0361218 | A1 | 11/2021 | Szabados et al. |
| 2021/0369178 | A1 | 12/2021 | Szabados et al. |
| 2021/0374502 | A1 | 12/2021 | Roth et al. |
| 2021/0378579 | A1 | 12/2021 | Doron et al. |
| 2021/0393187 | A1 | 12/2021 | Amos et al. |
| 2022/0022798 | A1 | 1/2022 | Soon-Shiong et al. |
| 2022/0031223 | A1 | 2/2022 | Li et al. |
| 2022/0039719 | A1 | 2/2022 | Abercrombie, II et al. |
| 2022/0039720 | A1 | 2/2022 | Abercrombie, II et al. |
| 2022/0039721 | A1 | 2/2022 | Abercrombie, II et al. |
| 2022/0039722 | A1 | 2/2022 | Abercrombie, II et al. |
| 2022/0079497 | A1 | 3/2022 | Bardy et al. |
| 2022/0093247 | A1 | 3/2022 | Park et al. |
| 2022/0095982 | A1 | 3/2022 | de Saint Victor et al. |
| 2022/0142493 | A1 | 5/2022 | Albert |
| 2022/0142495 | A1 | 5/2022 | De Marco et al. |
| 2022/0160279 | A1 | 5/2022 | Abercrombie, II et al. |
| 2022/0160285 | A1 | 5/2022 | Szabados et al. |
| 2022/0167905 | A1 | 6/2022 | Szabados et al. |
| 2022/0280093 | A1 | 9/2022 | Abercrombie, II et al. |
| 2022/0296144 | A1 | 9/2022 | Abercrombie, II et al. |
| 2022/0330874 | A1 | 10/2022 | Szabados et al. |
| 2022/0330875 | A1 | 10/2022 | Szabados et al. |
| 2022/0361793 | A1 | 11/2022 | Abercrombie, II et al. |
| 2023/0056777 | A1 | 2/2023 | Abercrombie, II et al. |
| 2023/0172511 | A1 | 6/2023 | Abercrombie, II et al. |
| 2023/0172518 | A1 | 6/2023 | Szabados et al. |
| 2023/0200702 | A1 | 6/2023 | Sepulveda et al. |
| 2023/0207122 | A1 | 6/2023 | Park et al. |
| 2023/0248288 | A1 | 8/2023 | Bahney et al. |
| 2023/0371873 | A1 | 11/2023 | Abercrombie, II et al. |
| 2023/0371874 | A1 | 11/2023 | Abercrombie, II et al. |
| 2024/0145080 | A1 | 5/2024 | Park et al. |
| 2024/0321455 | A1 | 9/2024 | Hytopoulos et al. |
| 2024/0331875 | A1 | 10/2024 | Hytopoulos et al. |
| 2024/0358310 | A1 | 10/2024 | Szabados et al. |
| 2024/0382130 | A1 | 11/2024 | Bahney et al. |
| 2024/0382131 | A1 | 11/2024 | Bahney et al. |
| 2024/0398309 | A1 | 12/2024 | Kumar et al. |
| 2024/0398310 | A1 | 12/2024 | Kumar et al. |
| 2025/0009271 | A1 | 1/2025 | Bahney et al. |
| 2025/0057459 | A1 | 2/2025 | Kumar et al. |

FOREIGN PATENT DOCUMENTS

| | | |
|---|---|---|
| AU | 2021218704 | 2/2024 |
| CA | 2 752 154 | 8/2010 |
| CA | 2 898 626 | 7/2014 |
| CA | 2 797 980 | 8/2015 |
| CA | 2 651 203 | 9/2017 |
| CA | 2 966 182 | 6/2020 |
| CA | 3 171 482 | 3/2024 |
| CN | 102038497 | 7/2012 |
| CN | 102883775 | 12/2014 |
| CN | 103997955 | 11/2016 |
| CN | 303936805 | 11/2016 |
| CN | 106456984 | 2/2017 |
| CN | 107205679 | 9/2017 |
| CN | 107708991 | 2/2018 |
| CN | 108113647 | 6/2018 |
| CN | 108135929 | 6/2018 |
| CN | 109363659 | 2/2019 |
| CN | 110491500 | 11/2019 |
| CN | 110766691 | 2/2020 |
| CN | 110890155 | 3/2020 |
| CN | 110974217 | 4/2020 |
| CN | 115426940 | 12/2022 |
| CN | 116322498 | 6/2023 |
| CN | 116530951 | 8/2023 |
| EM | 001857966-0001 | 5/2011 |
| EM | 003611714-0001 | 1/2017 |
| EM | 003611714-0002 | 1/2017 |
| EM | 003611714-0003 | 1/2017 |
| EM | 003611714-0004 | 1/2017 |
| EM | 003611714-0005 | 1/2017 |
| EP | 0509689 | 4/1992 |
| EP | 1738686 | 6/2006 |
| EP | 1782729 | 5/2007 |
| EP | 1981402 | 10/2008 |
| EP | 2262419 | 12/2010 |
| EP | 2395911 | 12/2011 |
| EP | 2568878 | 3/2013 |
| EP | 2635179 | 9/2013 |
| EP | 2635180 | 9/2013 |
| EP | 2948050 | 12/2015 |
| EP | 2983593 | 2/2016 |
| EP | 3165161 | 5/2017 |
| EP | 3212061 | 9/2017 |
| EP | 3753483 | 12/2020 |
| EP | 3387991 | 6/2022 |
| EP | 4103051 | 12/2022 |
| GB | 2 299 038 | 9/1996 |
| GB | 2 348 707 | 10/2000 |
| IN | 002592907-0001 | 12/2014 |
| JP | S61-137539 | 6/1986 |
| JP | H05-329123 | 12/1993 |
| JP | H08-317913 | 3/1996 |
| JP | H08-322952 | 12/1996 |
| JP | 2000-126145 | 5/2000 |
| JP | 2001-057967 | 3/2001 |
| JP | 2003-275186 | 9/2003 |
| JP | 2004-121360 | 4/2004 |
| JP | 2006-110180 | 4/2006 |
| JP | 2006-136405 | 6/2006 |
| JP | 2006-520657 | 9/2006 |
| JP | 2007-045967 | 2/2007 |
| JP | 2007-503910 | 3/2007 |
| JP | 2007-504917 | 3/2007 |
| JP | 2007-097822 | 4/2007 |
| JP | 2007-296266 | 11/2007 |
| JP | 2008-532596 | 8/2008 |
| JP | 2008-200120 | 9/2008 |
| JP | 2009-518099 | 5/2009 |
| JP | 2009-525816 | 7/2009 |
| JP | 2011-516110 | 5/2011 |
| JP | 2011-519583 | 7/2011 |
| JP | 2013-521966 | 6/2013 |
| JP | 5203973 | 6/2013 |
| JP | 2013-531512 | 8/2013 |
| JP | 1483906 S | 10/2013 |
| JP | 2014-008166 | 1/2014 |
| JP | 5559425 | 7/2014 |
| JP | 2014-150826 | 8/2014 |
| JP | 2014-236982 | 12/2014 |
| JP | 2015-530225 | 10/2015 |
| JP | 2015-531954 | 11/2015 |
| JP | 2016-504159 | 2/2016 |
| JP | 2013-517053 | 5/2016 |
| JP | 2016-523139 | 8/2016 |
| JP | 2017-136380 | 8/2017 |
| JP | 6198849 | 9/2017 |
| JP | 2017-209482 | 11/2017 |
| JP | 2018-504148 | 2/2018 |
| JP | 2018-508325 | 3/2018 |
| JP | 2018-513702 | 5/2018 |
| JP | 6336640 | 5/2018 |
| JP | D1596476 | 8/2018 |
| JP | 2018-153651 | 10/2018 |
| JP | 2018-174995 | 11/2018 |
| JP | 2019-503761 | 2/2019 |
| JP | 6491826 | 3/2019 |
| JP | 6495228 | 3/2019 |
| JP | 2019-140680 | 8/2019 |

(56) References Cited

FOREIGN PATENT DOCUMENTS

| | | |
|---|---|---|
| JP | 2019-528511 | 10/2019 |
| JP | 2020-058819 | 4/2020 |
| JP | 2020-509840 | 4/2020 |
| JP | 6766199 | 9/2020 |
| JP | 2021-003591 | 1/2021 |
| JP | 6901543 | 6/2021 |
| JP | 2021-525616 | 9/2021 |
| JP | 2021-166726 | 10/2021 |
| JP | 2022-501123 | 1/2022 |
| JP | 2022-037153 | 3/2022 |
| JP | 2022-038858 | 3/2022 |
| JP | 2022-126807 | 8/2022 |
| JP | 2023-508235 | 3/2023 |
| JP | 2023-074267 | 5/2023 |
| JP | 2023-100210 | 7/2023 |
| JP | 2023-536981 | 8/2023 |
| JP | 2023-536982 | 8/2023 |
| JP | 7406001 | 12/2023 |
| JP | 2024-009608 | 1/2024 |
| JP | 2024-502335 | 1/2024 |
| JP | 2024-021061 | 2/2024 |
| JP | 2024-026058 | 2/2024 |
| JP | 7431777 | 2/2024 |
| JP | 2024-050777 | 4/2024 |
| JP | 2024-521799 | 6/2024 |
| JP | 2024-087811 | 7/2024 |
| JP | 2024-104034 | 8/2024 |
| JP | 7551696 | 9/2024 |
| JP | 2024-164285 | 11/2024 |
| JP | 2025-000653 | 1/2025 |
| JP | 2025-500035 | 1/2025 |
| KR | 3003784570000 | 3/2005 |
| KR | 1020050055072 | 6/2005 |
| KR | 1020140050374 | 4/2014 |
| KR | 10-1513288 | 4/2015 |
| KR | 3008476060000 | 3/2016 |
| KR | 3008476090000 | 3/2016 |
| KR | 3008482960000 | 3/2016 |
| KR | 3008584120000 | 6/2016 |
| KR | 3008953750000 | 2/2017 |
| KR | 3008953760000 | 2/2017 |
| KR | 3008987790000 | 3/2017 |
| KR | 1020170133527 | 12/2017 |
| KR | 3009445870000 | 2/2018 |
| KR | 3009547690000 | 4/2018 |
| KR | 3009547710000 | 4/2018 |
| KR | 10-2019-0114694 | 10/2019 |
| KR | 10-2563372 | 7/2023 |
| KR | 10-2023-0119036 | 8/2023 |
| KR | 10-2024-0116830 | 7/2024 |
| WO | WO 87/01024 | 2/1987 |
| WO | WO 99/023943 | 5/1999 |
| WO | WO 01/016607 | 3/2001 |
| WO | WO 2003/043494 | 5/2003 |
| WO | WO 2004/100785 | 11/2004 |
| WO | WO 2005/025668 | 3/2005 |
| WO | WO 2005/037946 | 4/2005 |
| WO | WO 2005/084533 | 9/2005 |
| WO | WO 2006/094513 | 9/2006 |
| WO | WO 2007/049080 | 3/2007 |
| WO | WO 2007/036748 | 4/2007 |
| WO | WO 2007/063436 | 6/2007 |
| WO | WO 2007/066270 | 6/2007 |
| WO | WO 2007/071180 | 6/2007 |
| WO | WO 2007/072069 | 6/2007 |
| WO | WO 2007/092543 | 8/2007 |
| WO | WO 2008/005015 | 1/2008 |
| WO | WO 2008/005016 | 1/2008 |
| WO | WO 2008/057884 | 5/2008 |
| WO | WO 2008/120154 | 10/2008 |
| WO | WO 2009/055397 | 4/2009 |
| WO | WO 2009/074928 | 6/2009 |
| WO | WO 2009/112972 | 9/2009 |
| WO | WO 2009/112976 | 9/2009 |
| WO | WO 2009/112979 | 9/2009 |
| WO | WO 2009/134826 | 11/2009 |
| WO | WO 2010/014490 | 2/2010 |
| WO | WO 2010/104952 | 9/2010 |
| WO | WO 2010/105203 | 9/2010 |
| WO | WO 2010/107913 | 9/2010 |
| WO | WO 2010/093900 | 10/2010 |
| WO | WO 2011/077097 | 6/2011 |
| WO | WO 2011/084636 | 7/2011 |
| WO | WO 2011/112420 | 9/2011 |
| WO | WO 2011/143490 | 11/2011 |
| WO | WO 2011/149755 | 12/2011 |
| WO | WO 2012/003840 | 1/2012 |
| WO | WO 2012/009453 | 1/2012 |
| WO | WO 2012/061509 | 5/2012 |
| WO | WO 2012/061518 | 5/2012 |
| WO | WO 2012/125425 | 9/2012 |
| WO | WO 2012/140559 | 10/2012 |
| WO | WO 2012/160550 | 11/2012 |
| WO | WO 2013/065147 | 5/2013 |
| WO | WO 2013/179368 | 12/2013 |
| WO | WO 2014/047032 | 3/2014 |
| WO | WO 2014/047205 | 3/2014 |
| WO | WO 2014/051563 | 4/2014 |
| WO | WO 2014/055994 | 4/2014 |
| WO | WO 2014/116825 | 7/2014 |
| WO | WO 2014/168841 | 10/2014 |
| WO | WO 2014/197822 | 12/2014 |
| WO | WO 2015/089484 | 6/2015 |
| WO | WO 2016/044514 | 3/2016 |
| WO | WO 2016/044515 | 3/2016 |
| WO | WO 2016/044519 | 3/2016 |
| WO | WO 2016/057728 | 4/2016 |
| WO | WO 2016/070128 | 5/2016 |
| WO | WO 2016/130545 | 8/2016 |
| WO | WO 2016/172201 | 10/2016 |
| WO | WO 2016/181321 | 11/2016 |
| WO | WO 2017/039518 | 3/2017 |
| WO | WO 2017/041014 | 3/2017 |
| WO | WO 2017/043597 | 3/2017 |
| WO | WO 2017/043603 | 3/2017 |
| WO | WO 2017/108215 | 6/2017 |
| WO | WO 2017/159635 | 9/2017 |
| WO | WO 2018/164840 | 9/2018 |
| WO | WO 2018/218310 | 12/2018 |
| WO | WO 2019/070978 | 4/2019 |
| WO | WO 2019/071201 | 4/2019 |
| WO | WO 2019/188311 | 10/2019 |
| WO | WO 2019/191487 | 10/2019 |
| WO | WO 2019/233807 | 12/2019 |
| WO | WO 2020/008864 | 1/2020 |
| WO | WO 2020/013895 | 1/2020 |
| WO | WO 2020/041363 | 2/2020 |
| WO | WO 2020/058314 | 3/2020 |
| WO | WO 2020/224041 | 11/2020 |
| WO | WO 2020/0226852 | 11/2020 |
| WO | WO 2020/262403 | 12/2020 |
| WO | WO 2021/150122 | 7/2021 |
| WO | WO 2021/163331 | 8/2021 |
| WO | WO 2021/200245 | 10/2021 |
| WO | WO 2021/200764 | 10/2021 |
| WO | WO 2021/205788 | 10/2021 |
| WO | WO 2021/210592 | 10/2021 |
| WO | WO 2021/241308 | 12/2021 |
| WO | WO 2021/245203 | 12/2021 |
| WO | WO 2022/034045 | 2/2022 |
| WO | WO 2022/093709 | 5/2022 |
| WO | WO 2022/147520 | 7/2022 |
| WO | WO 2022/251636 | 12/2022 |
| WO | WO 2023/114742 | 6/2023 |
| WO | WO 2024/102663 A2 | 5/2024 |

OTHER PUBLICATIONS

AAMI, "Ambulatory electrocardiographs," American National Standards Institute, Inc. Oct. 29, 1998, in 67 pages.

AAMI, "Cardiac monitors, heart rate meters, and alarms," American National Standards Institute, Inc., May 6, 2002, in 87 pages.

(56) References Cited

OTHER PUBLICATIONS

ACLS Medical Training, "The Basics of ECG," retrieved from URL: https://www.aclsmedicaltraining.com/basics-of-ecg/, in 3 pages.
Adamec et al., "ECG Holter: Guide to Electrocardiographic Interpretation," Springer Science Business Media, LLC, in 9 pages.
AlGhatrif et al., "A brief review: history to understand fundamentals of electrocardiography," CoActrion, Apr. 30, 2012, in 5 pages.
Ashley et al., "Cardiology Explained," Remedica, 2004, retreieved from URL: https://www.ncbi.nlm.nih.gov/books/NBK2204/?report=printable, in 4 pages.
Cadogan, "Norman J. Holter," Life in the Fastlane, Jul. 27, 2022 in 8 pages.
Chung, "Ambulatory Electrocardiography," Springer-Veriag New York Inc., 1979 in 25 pages.
Crawford et al., "ACC/AHA Guidelines for Ambulatory Electrocardiography: Executive Summary and Recommendations," American College of Cardiology / American Heart Association, Aug. 24, 1999, in 20 pages.
Dexcom STS Sensor, "Instructions for Use," in 51 pages.
Grant, "Spatial Vector Electrocardiography: A method for Calculating the Spatial Electrical Vectors of the Heart from Conventional Leads," Circulation, vol. 11, Nov. 1950, in 20 pages.
Harland et al., "Electric potential probes—new directions in the remote sensing of the human body," Institute of Physics Publishing, Dec. 21, 2001, pp. 163-169.
Hubner, "Which Disposable Chest Electrode?" British Medical Journal, 1969, pp. 507-510.
Kalahasty et al., "A Brief History of Remote Cardiac Monitoring," Virginia Commonwealth University School of Medicine and VCUHS Medical Center, 2013 in 8 pages.
Khandpur, "Printed Circuit Boards: Design, Fabrication, Assembly and Testing," McGraw-Hill, 2006, in 43 pages.
Morganroth, "Ambulatory Holter Electrocardiography: Choice of Technologies and Clinical Uses," Annais of Internal Medicine, vol. 102, No. 1, Jan. 1985, in 9 pages.
National Library of Medicine, "In brief: What is an electrocardiogram (ECG)?" Jun. 6, 2023, retrieved from URL: https://www.ncbi.nlm.nih.gov/books/NBK536878/ in 4 pages.
Prutchi et al., "Design and Development of Medical Electronic Instrumentation: A Practical Perspective of the Design, Construction, and Test of Medical Devices," Wiley-Interscience, 2005 in 6 pages.
Thakor, "From Holter Monitors to Automatic Defibrillators: Developments in Ambulatory Arrhythmia Monitoring," IEEE Transactions on Biomedical Engineering, vol. BME-31, No. 12, Dec. 1984, in 9 pages.
Trend et al., "Are ECG Welsh cup electrodes effectively cleaned?" Journal of Hospital Infection, 1989, pp. 325-331.
Young et al., "University Physics," Sears & Zemansky, Fifteenth Edition, in 8 pages.
3M Corporation, "3M Surgical Tapes—Choose the Correct Tape" quicksheet (2004).
Akram, Muhammad Usman, "Application of Prototype Based Fuzzy Classifiers for ECG based Cardiac Arrhythmia Recognition", Jan. 1, 2008 retrieved from faculty.pieas.edu.pk/Fayyaz/_static/pubfiles/student/usman_thesis.pdf [retrieved on Feb. 17, 2015] in 93 pages.
Altini, et al., An ECG Patch Combining a Customized Ultra-Low-Power ECG SOC Withbluetooth Low Energy for Long Term Ambulatory Monitoring, Conference: Proceddings of Wireless Health 2011, WH 2011, Oct. 10-13, 2011.
Behind the Design: How iRhythm Built Its New Zio Monitor. Online, published date Oct. 4, 2023.Retrieved on Jun. 18, 2024 from URL: https://www.mddionline.com/cardiovascular/behind-the-design-how-irhythm-built-its-new-zio-monitor.
British-Made Early Warning Monitor a "Game Changer", healthcare-in-europe.com, Mar. 31, 2014.
Comstock, Proteus Digital Health Quietly Launches Consumer-Facing Wearable for Athletes, Mobile Health News, Oct. 29, 2014.
Coxworth, Small Adhesive Partch Outperforms Traditional Tech for Detecting Arrhythmia, Scripps, iRhythm Technologies, Jan. 3, 2014.

Del Mar et al.; The history of clinical holter monitoring; A.N.E.; vol. 10; No. 2; pp. 226-230; Apr. 2005.
Enseleit et al.; Long-term continuous external electrocardiographic recording: a review; Europsace; vol. 8; pp. 255-266; 2006.
Feng-Tso Sun et al., "PEAR: Power efficiency through activity recognition (for ECG-based sensing)", Pervasive Computing Technologies for Healthcare (PervasiveHealth) 2011 5th International Conference on, IEEE, May 23, 2011. pp. 115-122.
Hoefman et al.; Optimal duration of event recording for diagnosis of arrhythmias in patients with palpitations and light-headedness in the general practice; Family Practice; Dec. 7, 2006.
Huyett "Keystock & Shim Stock Catalog" p. Feb. 9, 2014. found at https://issuu.com/glhuyett/docs/gl-huyett-keystock-catalog/20 (Year: 2014).
Ikeda Y. et al., "A Method for Transmission Data Reduction for Automated Monitoring System via CNN Distribution Process", Proceedings of the Symposium of Multi-media, Distribution, Coordination, and Mobile (DOCOMO2019), Jul. 2019.
International Preliminary Report on Patentability and Written Opinion in PCT Application No. PCT/US2011/036335, dated Nov. 22, 2012.
International Search Report and Written Opinion in PCT Application No. PCT/US2011/036335, dated Oct. 31, 2011.
Kennedy et al.; The history, science, and innovation of holter technology; A.N.E.; vol. 11; No. 1; pp. 85-94; 2006.
"Mayo Alumni", Mayo Clinic, Rochester, MN, Spring 2011, in 24 pages.
Medtronic Launches SEEQ Wearable Cardiac Monitoring System in United States, Diagnostic and Interventional Cardiology, Oct. 7, 2014.
Mundt et al. "A Multiparameter Wearable Physiologic Monitoring System for Space and Terrestrial Applications" IEEE Transactions on Information Technology in Biomedicine, vol. 9, No. 3, pp. 382-384, Sep. 2005.
Prakash, New Patch-Based Wearable Sensor Combines Advanced Skin Adhesives and Sensor Technologies, Advantage Business Marketing, Jul. 17, 2012.
Rajpurkar et al, "Cardiologist-Level Arrhythmia Detection with Convolutinal Neural Networks," ARXIV.org, https://arxiv.org/abs/1707.01836, Jul. 6, 2017 in 9 pages.
Redjem Bouhenguel et al, "A risk and Incidence Based Atrial Fibrillation Detection Scheme for Wearable Healthcare Computing Devices," Pervasive Computer Technologies for Healthcare, 2012 6th International Conference on, IEEE, pp. 97-104, May 21, 2012.
Reiffel et al.; Comparison of autotriggered memory loop recorders versus standard loop recorders versus 24-hour holter monitors for arrhythmia detection; Am. J. Cardiology; vol. 95; pp. 1055-1059; May 1, 2005.
Request for Reexamination of U.S. Pat. No. 7,020,508 under 35 U.S.C. §§ 311-318 and 37 C.F.R. § 1.913 as submitted Sep. 14, 2012 in 78 pages.
Scapa Medical product listing and descriptions (2008) available at http://www.caapana.com/productlist.jsp and http://www.metplus.co.rs/pdf/prospekti/Samolepljivemedicinsketrake.pdf; retrieved via WayBack Machine Sep. 24, 2012.
Strong, Wearable Technologies Conference 2013 Europe—Notes and Roundup, Wearable Technologies Conference, Feb. 8, 2013.
Sumner, Stanford Engineers Monitor Heart Health Using Paper-Thin Flexible 'Skin', Stanford Report, May 14, 2013.
Ward et al.; Assessment of the diagnostic value of 24-hour ambulatory electrocardiographic monitoring; Biotelemetry Patient monitoring; vol. 7; 1980.
YouTube.com, "Demonstration of Nintendo controller repair," https://www.youtube.com/watch?v=hzybDNChNeU, Aug. 2010.
Ziegler et al.; Comparison of continuous versus intermittent monitoring of atrial arrhythmias; Heart Rhythm; vol. 3; No. 12; pp. 1445-1452; Dec. 2006.
Zimetbaum et al.; The evolving role of ambulatory arrhythmia monitoring in general clinic practice; Ann. Intern. Med.; vol. 130; pp. 846-8556; 1999.
Zimetbaum et al.; Utility of patient-activated cardiac event recorders in general clinical practice; The Amer. J. of Cardiology; vol. 79; Feb. 1, 1997.

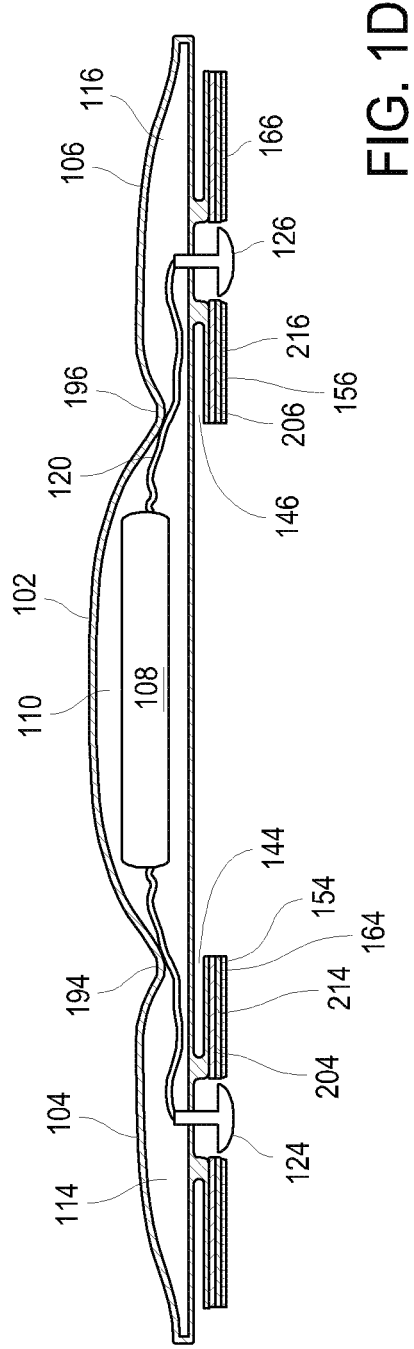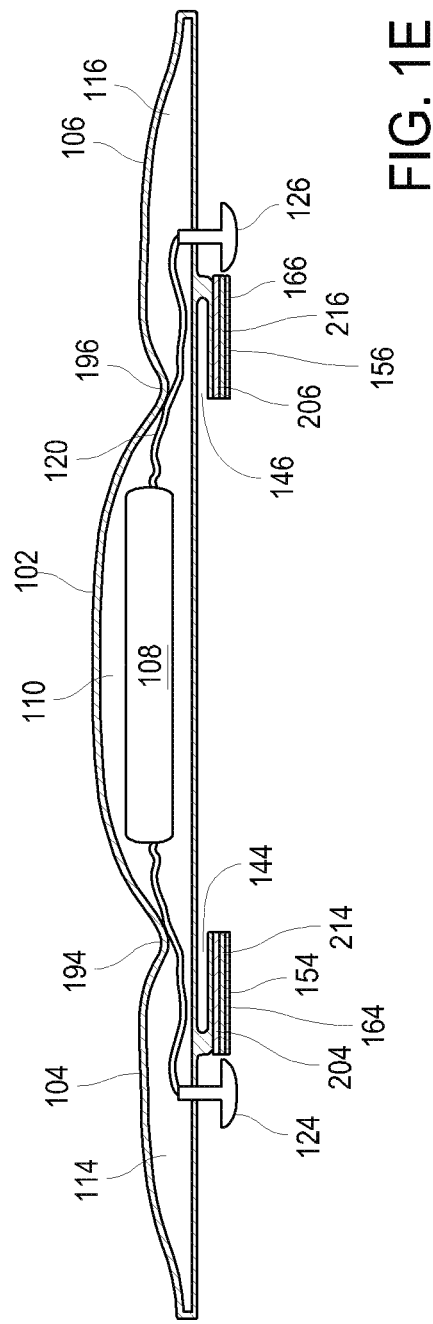

DEVICE FEATURES AND DESIGN ELEMENTS FOR LONG-TERM ADHESION

CROSS-REFERENCE TO RELATED APPLICATIONS

This application is a continuation of U.S. application Ser. No. 18/806,584, filed Aug. 15, 2024, titled "Device Features and Design Elements for Long-Term Adhesion" which claims priority to U.S. application Ser. No. 17/304,811, filed Jun. 25, 2021, titled "Device Features and Design Elements for Long-Term Adhesion" which claims priority to U.S. application Ser. No. 16/723,208, filed Dec. 20, 2019, titled "Device Features and Design Elements for Long-Term Adhesion" which claims priority to U.S. application Ser. No. 16/138,819, filed Sep. 21, 2018, titled "Device Features and Design Elements for Long-Term Adhesion" which claims priority to U.S. application Ser. No. 15/005,854, filed Jan. 25, 2016, titled "Device Features and Design Elements for Long-Term Adhesion" which claims priority to U.S. application Ser. No. 13/890,144, filed May 8, 2013, titled "Device Features and Design Elements for Long-Term Adhesion" which claims priority to U.S. application Ser. No. 13/563,546, filed Jul. 31, 2012, titled "Device Features and Design Elements for Long-Term Adhesion", which claims priority to U.S. patent application Ser. No. 13/106,750, filed May 12, 2011, which claims priority to U.S. Provisional Patent Application No. 61/334,081, filed May 12, 2010, entitled "Device Features and Design Elements for Long-Term Adhesion." All of the aforementioned applications are incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This application relates to devices worn on a body for monitoring, recording, reporting and/or treating the person wearing the device. Improvements in the device design elements and functionality are disclosed for maintaining the device in contact with and operational for extended periods of time, typically longer than 24 hours.

BACKGROUND OF THE INVENTION

The ability to adhere a medical device to a human body for a long-period of time is dependent on a variety of factors. In addition to the type and nature of the adhesive chosen, another factor is the mechanical design of the device. By design, this refers to, but is not limited to, the device shape, size, weight, flexibility, and rigidity. These design elements are influenced by a number of additional factors, including, hut not limited to, where on the body the device will attach and the duration of the attachment, moisture conditions in that area, movement conditions in that area, stretching and contraction in that area, interactions with external factors in that area such as clothing, and purposeful and/or inadvertent interaction between the person wearing the device and the device.

As many are typically used on the body for less than 24 hours, devices have not been designed that can withstand longer-term adhesion. Hence, there is a need to implement device features and design elements that have the ability to enhance the likelihood of adhesion of a device to a human body for 24 hours or more, while accommodating the functionality, shape, size, weight, flexibility, and rigidity of a given device.

SUMMARY

In one aspect of the invention, there is an electronic device for long-term adhesion to a mammal. The device has a housing containing an electronic component with a first wing and a second wing integrally formed with the housing. There is an electrode positioned on a bottom surface of each of the wings with the electrodes electrically connected to the electronic component. An adhesive layer is provided tor adhesion to a surface of the mammal. The adhesive layer is coated on a portion of the bottom surface of the wings. The adhesive layer is not coated on the electrode or on a bottom surface of the housing.

The electronic component in any of the devices described herein may include a processor having a memory with computer readable instructions to record signals from the first and second electrodes while the electronic device is attached to the mammal. The processor may be configured to only convert signals from the electrodes to digital signals, filter those signals and then store the signals in memory.

In another aspect, the device includes a flap connected to each of the wings. The flaps may extend below the housing. Additionally or alternatively, the adhesive layer is coated on a bottom surface of the flaps.

In another aspect, the device includes a connector segment In one aspect, the connector segment configured to connect the flaps together. In other aspects, the connector segment is located at least partially below the housing. Still further, the connector segment is not attached to the housing.

In one alternative, the adhesive layer is coated on a bottom surface of the flap.

In still another aspect, the adhesive for adhesion to a surface of the mammal is an adhesive that can absorb fluids. In another aspect, the adhesive that can absorb fluids is a hydrocolloid adhesive. In another aspect, the adhesive for adhesion to a surface of the mammal is a pressure-sensitive adhesive. The pressure sensitive adhesive is selected from the group consisting of: a polyacrylate, a polyisobutylene, and a polysiloxane. In one alternative, the device includes a diffusion barrier between the adhesive layer and each of the wings. The device may also include an additional adhesive layer and material layer between the wing and the adhesive layer for adhesion to the mammal. The material layer is configured to prevent diffusion of adhesive components from the adhesive layer to the wing. The diffusion barrier may be made from polyester or other suitable synthetic material.

In one aspect of the device, all or substantially all of the electronic components are within the housing. In another aspect, the wing is free from electronic components. In one aspect, the wing is more flexible than the housing. In one alternative, the wings and the housing are made from the same material. In another aspect, the wings and the housing are made from different materials. In another, the wings are made from a fabric. In still another aspect, the material used to make the wings includes a synthetic fiber. In another alternative, the wing and the flap are composed of the same material.

In another alternative, the device includes a hinge portion between the housing wmg, The hinge portion is configured to allow the device to bend between the housing and the wmg. In one aspect, the hinge portion exists between a rigid portion of the device and a flexible portion of the device. In one alternative, the rigid portion of the device corresponds to the portion of the housing including the electronics and the flexible portion of the device includes a wmg In one aspect, the bottom surface of the wing and the bottom surface of the flap are contiguous, In another aspect, the bottom surfaces of the wings, the flap, and the connectors are contiguous. In still other aspects, the flaps and the connector are contiguous.

In another aspect, the connector has at least one hole extending it. The hole may have any of a number of shapes such as circular, oval, round, or triangular.

In one aspect, the housing is thicker at a center of the housing than at edges of the housing.

In another aspect of the device, the housing is unattached to the mammal when the electrodes are in contact with the mammal.

In another alternative aspect of a device for long-term adhesion to a mammal, the device includes a housing with a first wing extending laterally from the housing and a second wing extending laterally from the housing without overlapping the first wing, There is a first electrode positioned on a bottom surface of the first wing and a second electrode positioned on a bottom surface of the second wing. An electronic memory is positioned within the housing. The electronic memory is configured to receive and store electronic signals from the first and second electrodes while the electronic device is attached to the mammal. There is also an adhesive layer on a portion of a bottom surface of the first wing and the second wing. The adhesive is not on a bottom surface of the housing. When the device is worn on the mammal, only the adhesive layer(s) are attached to the mammal.

In one aspect, the portion of the bottom surface of the first wing and the second wing does not include the first and second electrodes, In one device aspect, the first wing, the second wing, and the housing are formed from the same material. In still another, the first wing, the second wing and the housing integrally form a monolithic structure. In other aspects, an angle formed by the first wing, the second wing, and the housing is between approximately 90° and 180°, In one variation, the angle is approximately 180°, In another variation, the angle is approximately 135°.

In still other embodiments, there is a first hinged portion between the first electrode and the processor and a second hinged portion between the second electrode and the housing.

In a further aspect, at least a portion of the body uncovered is not adhered to the mammal when signals from the electrodes are being recorded in memory.

In another aspect, the device includes a first flap connected to the first wing medial to the first electrode and a second flap connected to the second wing medial to the second electrode. Each nap may extend below the housing.

The device may also include a connector segment configured to connect the flaps together. In one aspect, the connector segment is located at least partially below the housing, but is not attached to the housing.

In another aspect, there is an electronic device that has a patch including a housing containing an electronic component. There is an electrode positioned on a bottom surface of the patch, the electrode electrically connected to the electronic component. There is a first adhesive strip extending around the perimeter of the patch and a second adhesive strip extending around the perimeter of the first adhesive strip, In one aspect, the first adhesive cover over the first adhesive strip and a second adhesive cover over the second adhesive strip, The first and second adhesive covers may be configured to be separably removed from the first and second adhesive strips, In one alternative, the first adhesive strip extends between the first and second adhesive covers. In another alternative, the adhesive in the first and the second adhesive strips is an adhesive that can absorb fluids. In still another aspect, the adhesive that can absorb fluids is a hydrocolloid adhesive. In one alternative, the adhesive in the first and the second adhesive is a pressure-sensitive adhesive. In some aspects, the pressure-sensitive adhesive is a polyacrylate, a polyisobutylene, or a polysiloxane.

In one alternative, the second adhesive strip partially overlaps the first adhesive strip. In another aspect, the second adhesive strip is attached to a shell, the shell overlapping the first adhesive strip.

In still another alternative device for long-term adhesion to a mammal, the device includes a patch having a housing with an electronic component contained therein, There is an electrode positioned on a bottom surface of the patch, The electrode electrically connected to the electronic component There is a porous foam pad configured to he positioned between the electronic component and the mammal. In one aspect, the porous foam pad comprises a biocompatible foam material. In one variation, the porous foam pad can absorb fluids. In still another aspect, the porous foam pad is attached to the housing. In another, the porous foam pad is configured to be attached to the mammal. In another request, the porous foam pad can absorb fluids.

In one aspect of a method of applying an electronic device, there is a step of removing a first adhesive cover from the first wing of the electronic device to expose an electrode and an adhesive coated on a bottom surface of a first wing, There is a step of placing the exposed electrode into contact with the mammal by adhering the adhesive coated bottom of the first wing to the mammal. There is also a step of removing a second adhesive cover from the second wing of the electronic device to expose an adhesive coated on a bottom surface of the second wing and another exposed electrode, There is also a step of placing the another exposed electrode into contact with the mammal by adhering the adhesive coated bottom of the second wing to the mammal. After performing the removing and the placing steps, the housing is unattached to the mammal, but is held in position on the mammal using the adhesive coated bottoms of the first and the second wings.

In one alternative method of attaching a device, the electronic device includes a first nap connected to the first wing and a second flap connected to the second wing. The first and second flaps each extend below the housing. The step of removing a first adhesive cover from the first wing may also include exposing an adhesive coated on a bottom surface of the first flap. The step of removing a second adhesive cover from the second wing may also include exposing an adhesive coated on a bottom surface of the second flap.

In another alternative method of attaching a device, after performing the removing and the placing steps, the housing is held in position on the mammal using only the adhesive coated bottoms of the first wing, the second wing, the first flap and the second flap.

In an alternative aspect of a method of applying an electronic device to a mammal for long-term adhesion, the method includes removing a first adhesive cover from the first wing of the electronic device to expose an electrode and an adhesive coated on a bottom surface of the first wing.

There is also a step of removing a second adhesive cover from the second wing of the electronic device to expose an adhesive coated on a bottom surface of the second wing and another exposed electrode. There is a step of placing the exposed electrodes into contact with the mammal by adhering the adhesive coated on the bottom of the first and the second wings to the mammal, After performing the removing and the placing steps, the housing is unattached to the mammal, but is held in position on the mammal using the adhesive coated bottoms of the first and the second wings.

There is also provided a method of applying an electronic device to a mammal for long-term adhesion wherein the electronic device includes a patch. The patch includes an electronic component along with an electrode positioned on a bottom surface of the patch and electrically connected to the electronic component. There is a first adhesive strip extending around the perimeter of the patch and a second adhesive extending around the perimeter of the first adhesive strip. One aspect of a method of applying the device includes a step of removing an adhesive cover from the second adhesive strip of the electronic device. There is a step of applying pressure to the second adhesive strip to adhere the second adhesive strip to the mammal such that the electrode is in contact with the mammal. Then, after a period of time, removing an adhesive cover from the first adhesive strip of the electronic device. Next, there is the step of applying pressure to the first adhesive strip to adhere the first adhesive strip to the mammal such that the electrode remains in contact with the mammal.

In another alternative method of applying an electronic device to a mammal for long-term adhesion, the electronic device includes a patch, an electronic component, and an electrode positioned on a bottom surface of the patch and electrically connected to the electronic component. There is a first adhesive strip extending around the perimeter of the patch. The method includes a step of applying pressure to a first adhesive strip to adhere the first adhesive strip to the mammal such that the electrode is in contact with the mammal. After a period of time, placing a second adhesive strip around the perimeter of the first adhesive strip. Then there is the step of applying pressure to the second adhesive strip to adhere the second adhesive strip to the mammal such that the electrode remains in contact with the mammal.

Any of the above described devices may include additional aspects. A device may also include a first wire connecting the first electrode and the processor or an electronic memory and a second wire connecting the second electrode and the processor or an electronic memory. The first and second wires extend within the body and the first and second wings. In one aspect, the first and second wires extend within and are completely encapsulated within the body and the first and second wings. In one aspect, a conduit is provided within the body and the wings and the wires pass through the conduit. In one alternative, the conduit extends from the processor or electronic memory to an electrode so that the wire is completely within the conduit. In still other aspects of the devices described above, the first and second wires connecting the electrodes to the processor or electronics each include slack between the electrode and the processor. In one aspect, the slack is located in a portion of each wing that is configured to bed or flex. In another aspect, the slack is a portion of the wire within the wing and at least partially coiled about the first or the second electrode. In still other aspects, the slack is provided by a portion of the wire formed into a coil, a wave pattern, or a sinusoidal pattern along its length the connection point on the electronics to the connection point on the electrode.

In still other alternatives, the devices described above may be applied to any of a wide variety of conventional physiological data monitoring, recording and/or transmitting devices. Any of the improved adhesion design features and aspects may also be applied to conventional devices useful in the electronically controlled and/or time released delivery of pharmacological agents or blood testing, such as glucose monitors or other blood testing devices. Additional alternatives to the devices described may include the specific components of a particular application such as electronics, antenna, power supplies or charging connections, data ports or connections for down loading or off loading information from the device, adding or offloading fluids from the device, monitoring or sensing elements such as electrodes, probes or sensors or any other component or components needed in the device specific function. In still other aspects, the electronic component in any of the above devices is an electronic system configured for performing, with the electronic signals of the mammal detected by the electrodes, one or more or any combination of or the following electronic functions: monitoring, recording, analyzing, or processing using one or more algorithms electronic signals from the mammal. Stili further, any of the devices described above may include appropriate components such that the device is used to detect, record, process or transmit signals or information related to signals generated by a mammal to which the device is attached including but not limited to signals generated by one or more of EKG, EEG and/or EMG.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

Figure 1:
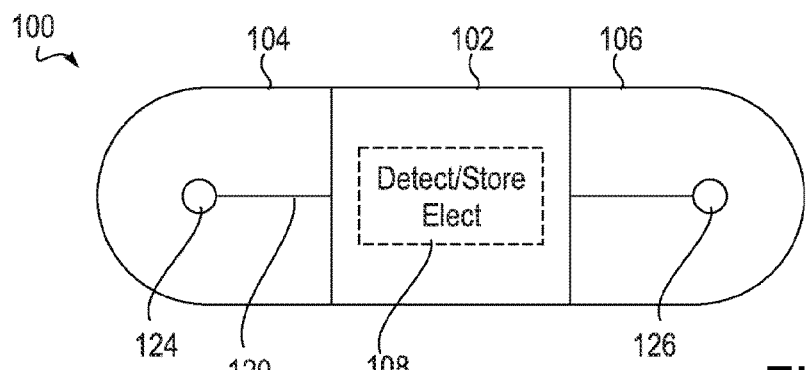
FIG. 1 is a top view of a patch having two wings.
Figure 1A:
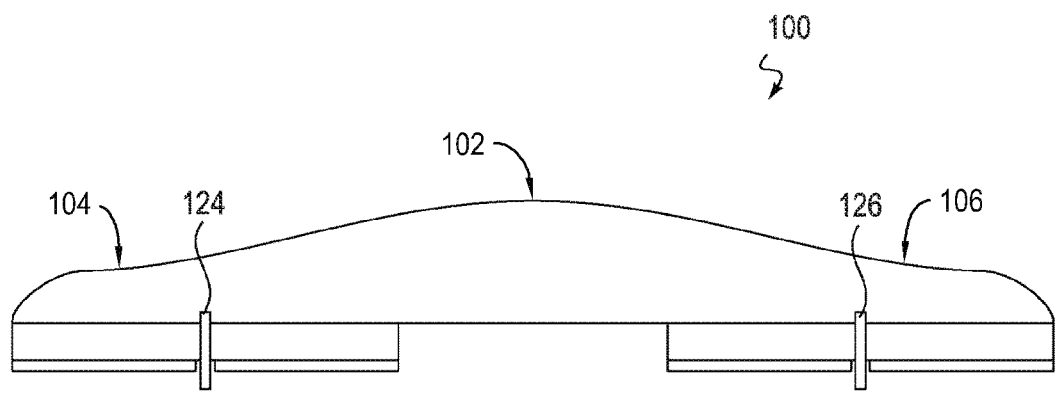
FIG. 1A is a representative cross-section of an embodiment of the patch in FIG. 1.
Figure 1B:
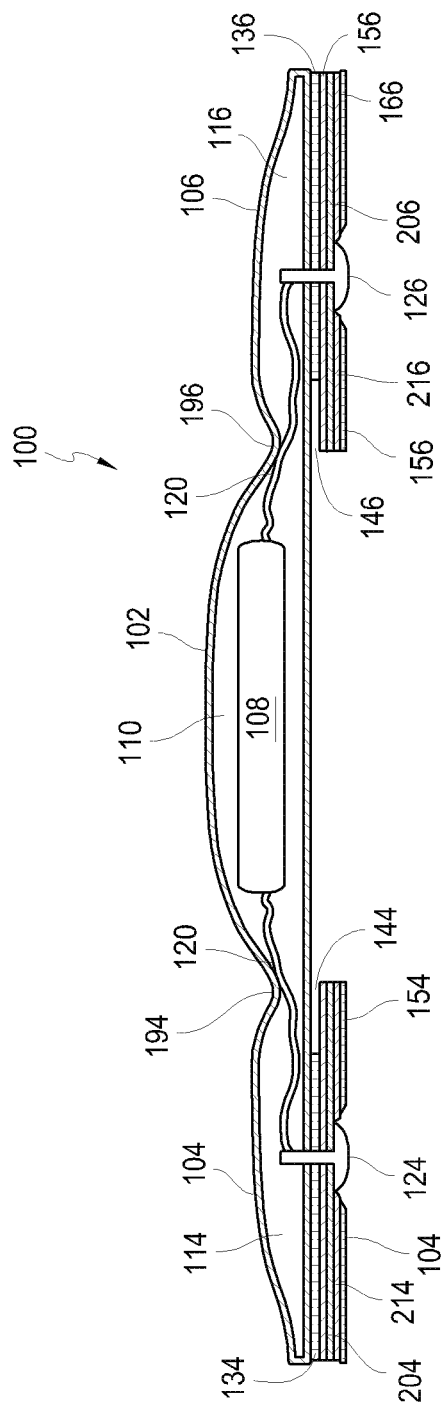
Figure 1C:
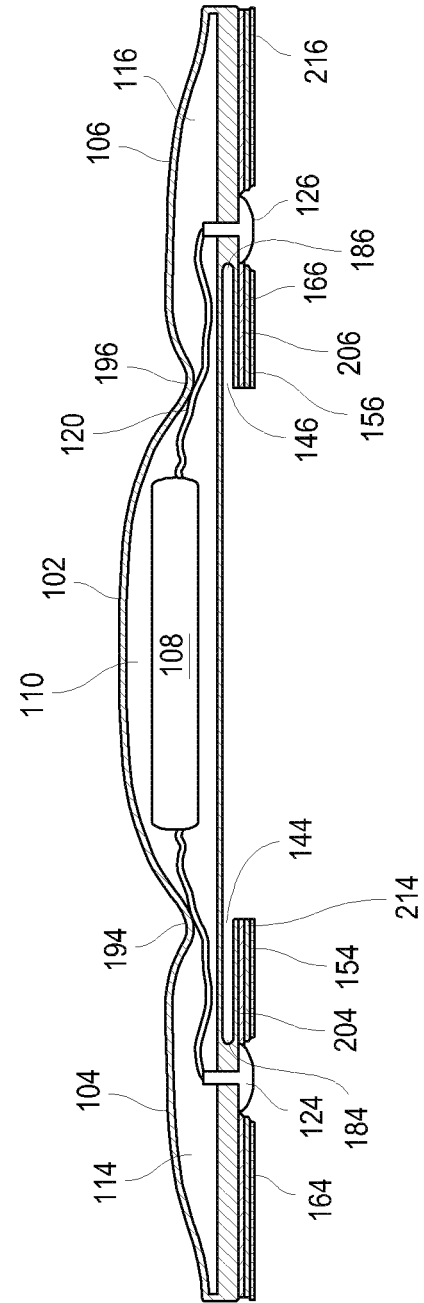

FIG. IB is a representative cross-section of another embodiment of the patch in FIG. 1;

FIG. 1C is a representative cross-section of another embodiment of the patch in

Figure 1F:
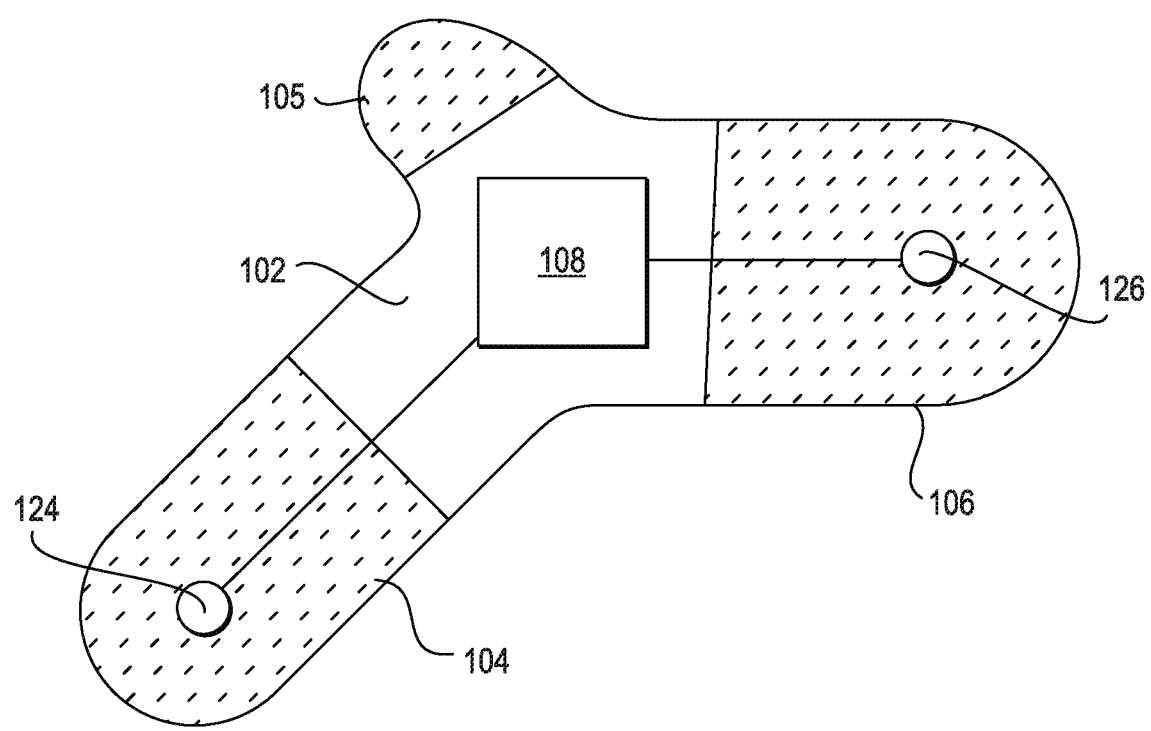
Figure 2A:
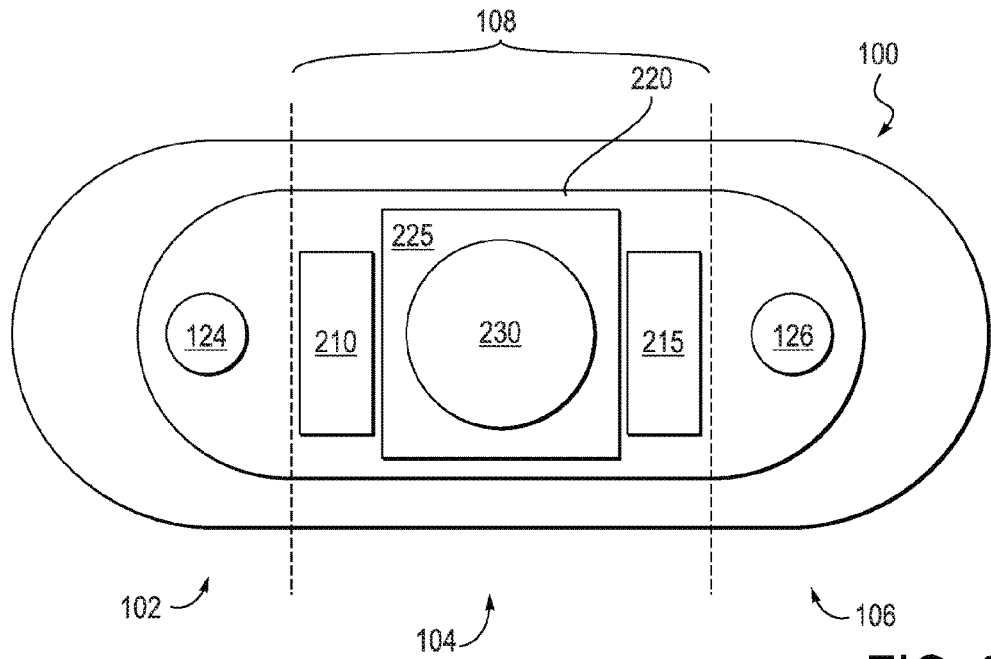
Figure 2B:
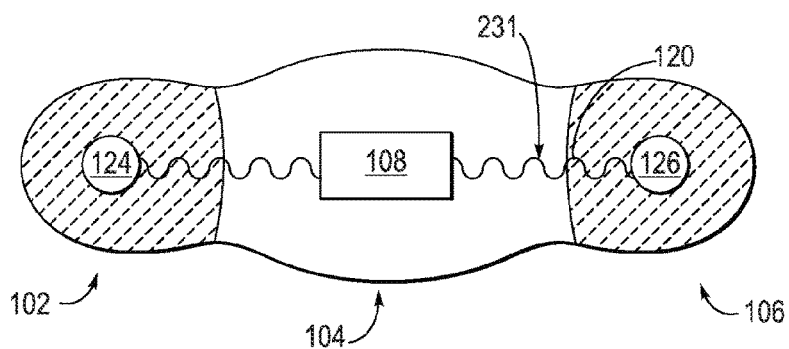
Figure 2C:
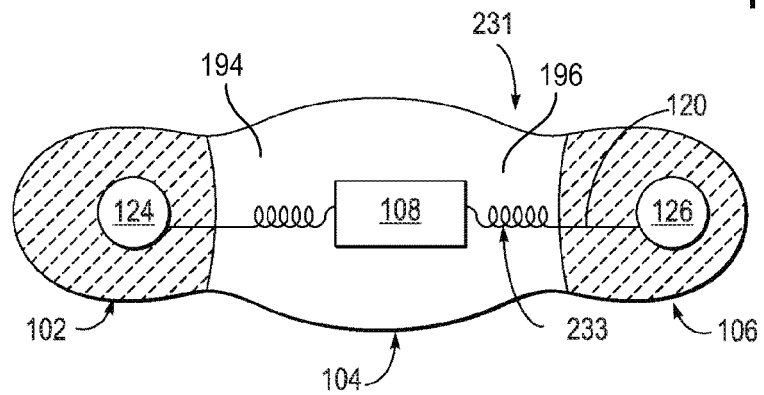
Figure 3:
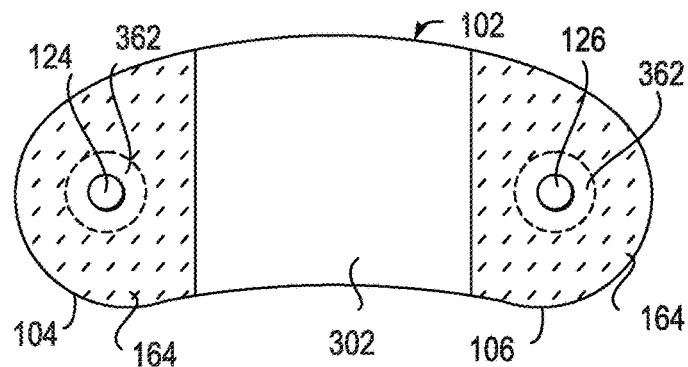
Figure 4A:
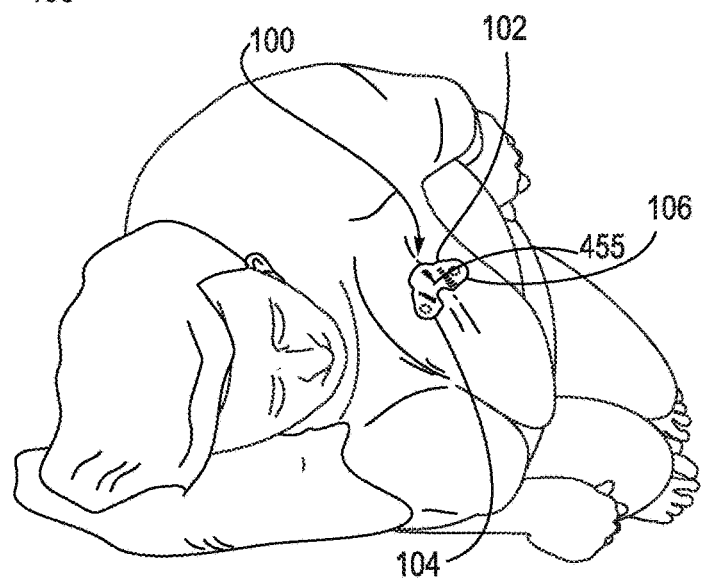
Figure 4B:
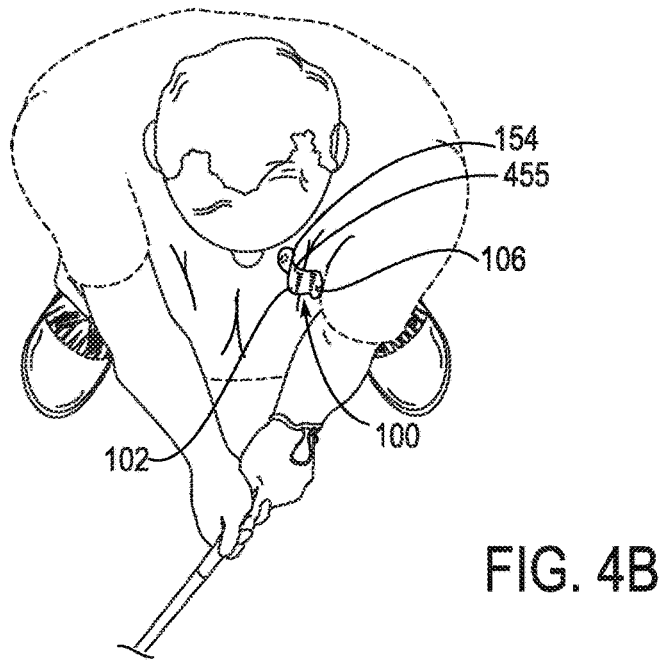
Figure 5A:
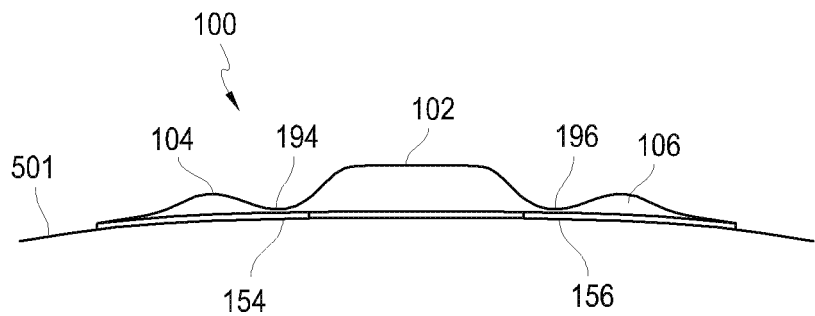
Figure 5B:
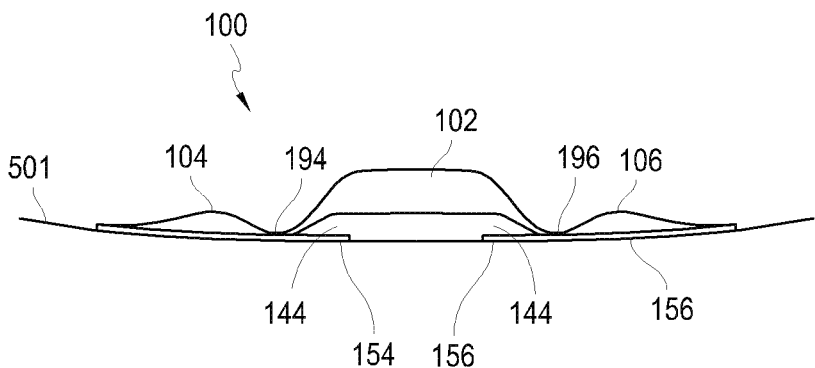
Figure 5C:
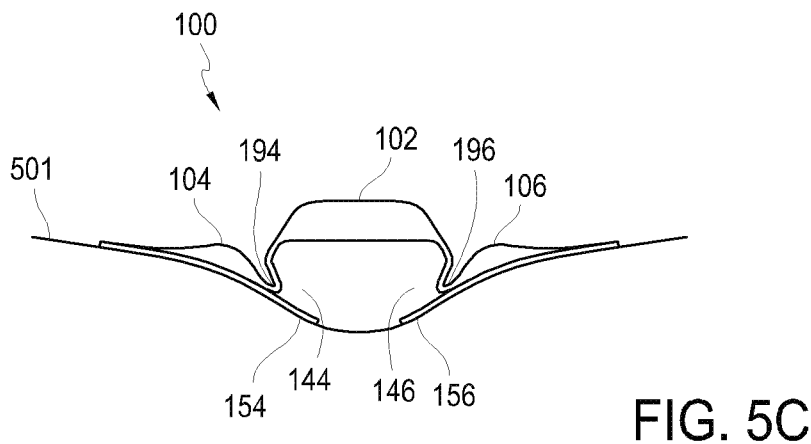
Figure 6A:
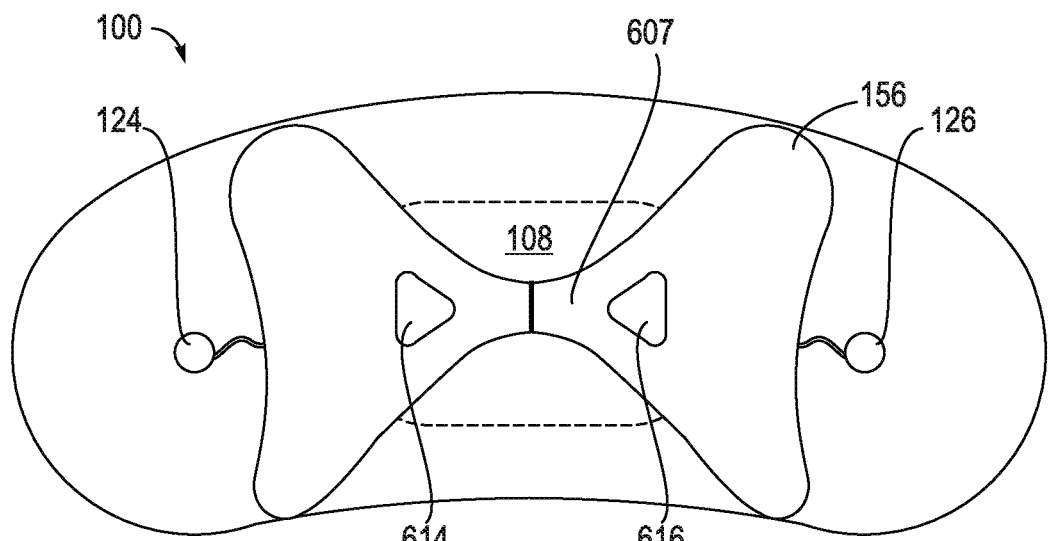
Figure 6B:
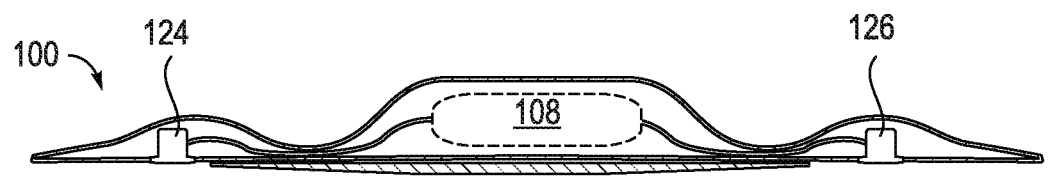
Figure 7A:
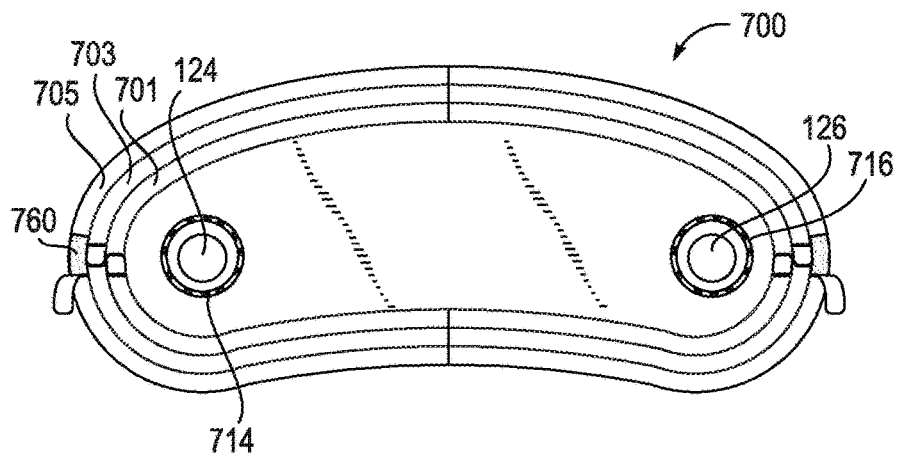
Figure 7B:
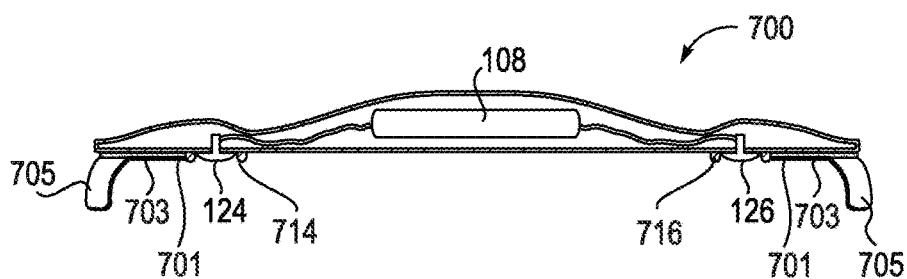
Figure 8A:
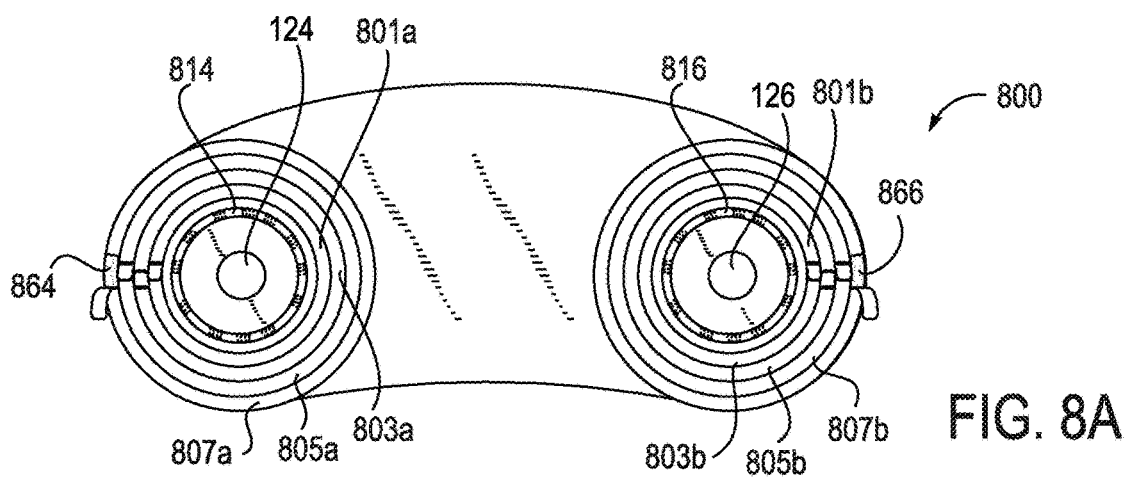
Figure 8B:
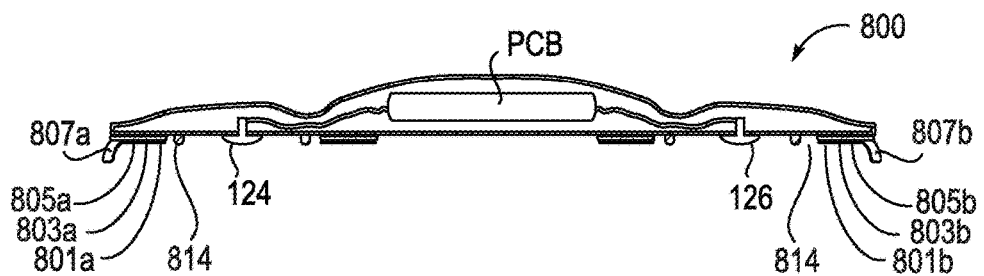
Figure 9A:
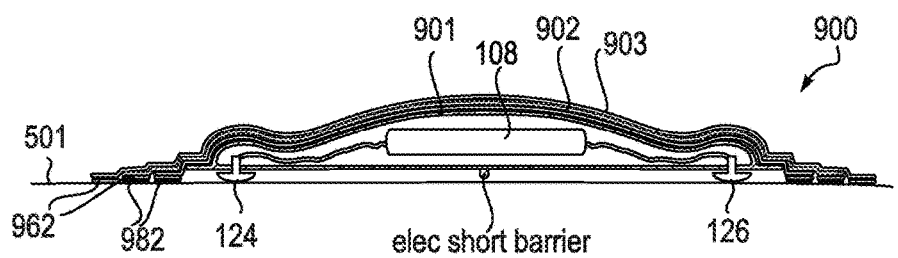
Figure 9B:
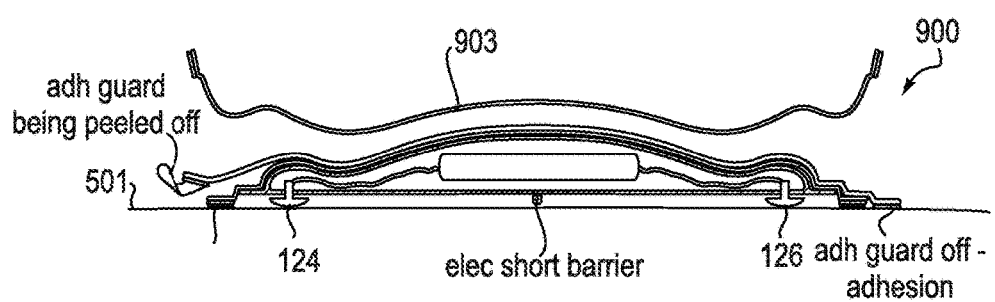
Figure 10A:
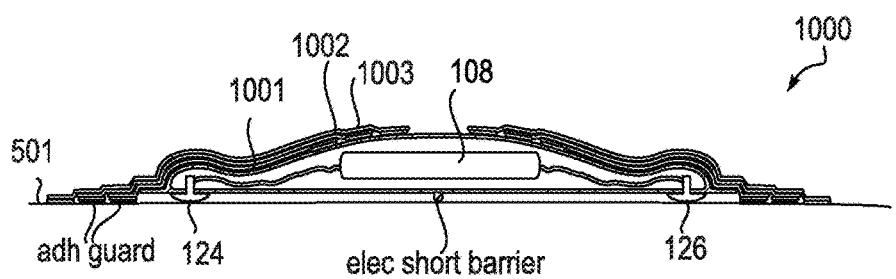
Figure 10B:
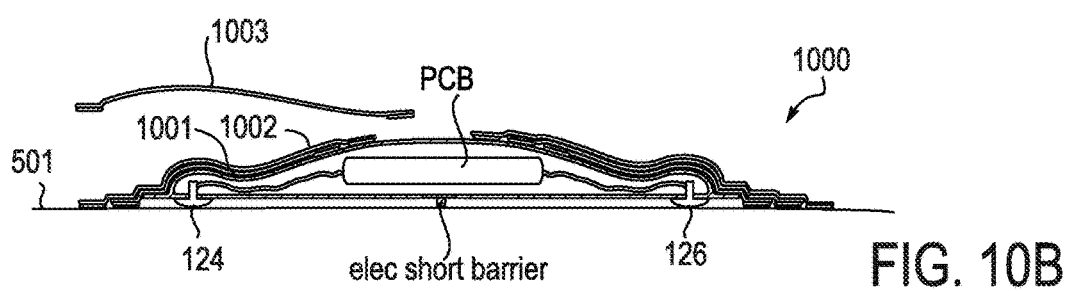
Figure 11:
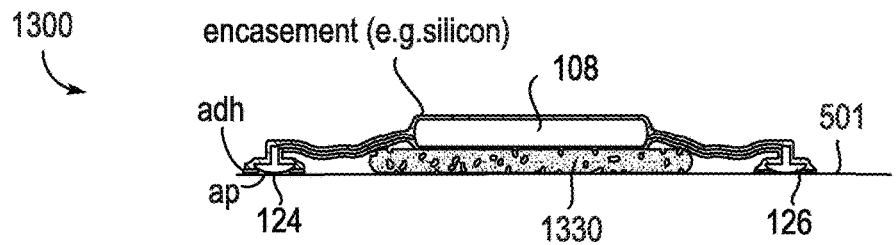
Figure 12:
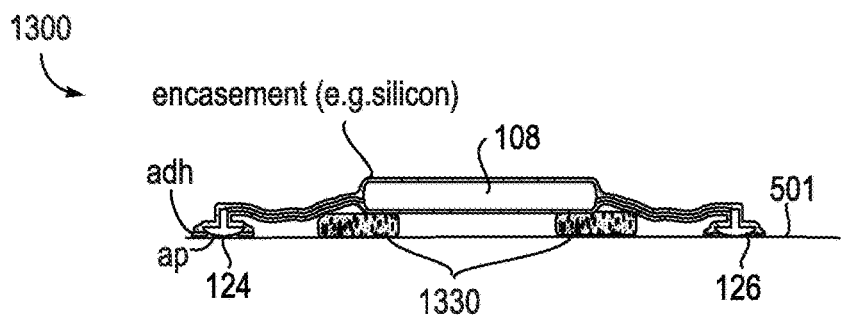
Figure 13A:
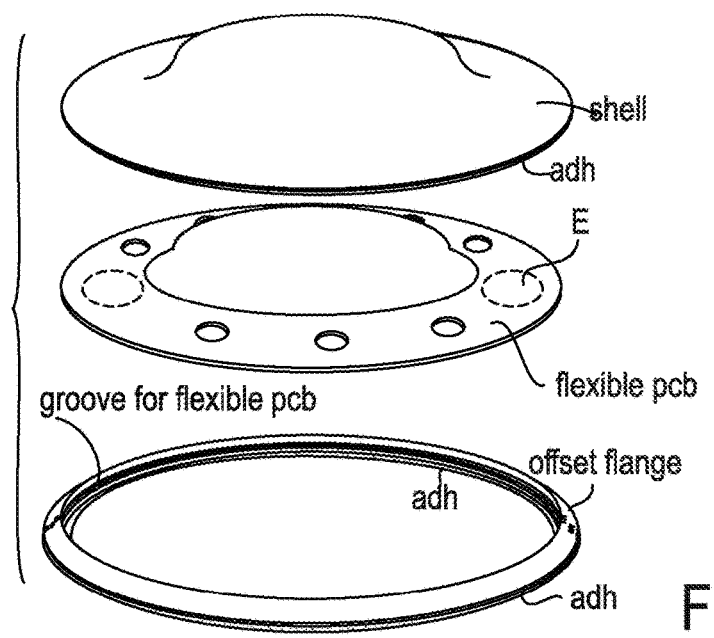

FIG. 1;

FIG. 1D is a representative cross-section of another embodiment of the patch in FIG. 1;

FIG. 1E is a representative cross-section of another embodiment of the patch in FIG. 1;

FIG. 1F is a top view of a patch having three wings illustrating an alternative electrode-electronics-electrode orientation;

FIG. 2A is a schematic drawing of the electronics contained within a patch;

FIG. 2B is a schematic drawing of a patch with wiring having slack in the form of undulations between electronics and electrodes;

FIG. 2C is a schematic drawing of a patch with wiring having slack in the form of a coil between electronics and electrodes;

FIG. 3 is the bottom view of a patch having adhesive thereon;

FIG. 4A shows a patch as worn by a person rolled to the side;

FIG. 4B shows a patch as worn by a person playing golf;

FIG. 5A shows a patch in response to a concave bend of the skin;

FIGS. 5B and 5C show a patch in response to a convex bend of the skin;

FIG. 6A is a bottom view of a patch having a connector between two flaps;

FIG. 6B is a cross-section of the patch of FIG. 6A;

FIG. 7A is a bottom view of a patch having multiple covers forming strips of adhesive;

FIG. 7B is a cross-section of the patch of FIG. 7A;

FIG. 8A is a bottom view of a patching having multiple covers forming strip of adhesive around each electrode;

FIG. 8B is a cross-section of the patch of FIG. 8A;

FIGS. 9A and 9B show a patch having multiple layers formed thereon;

FIGS. 10A and 10B show a patching having multiple layers formed thereon, each layer having multiple patches of adhesive;

FIG. 11 shows a patch having an open cell support;

FIG. 12 shows a patch having an annular open cell support;

FIG. 13A shows a patch having a protective shell thereon; and

Figure 13B:
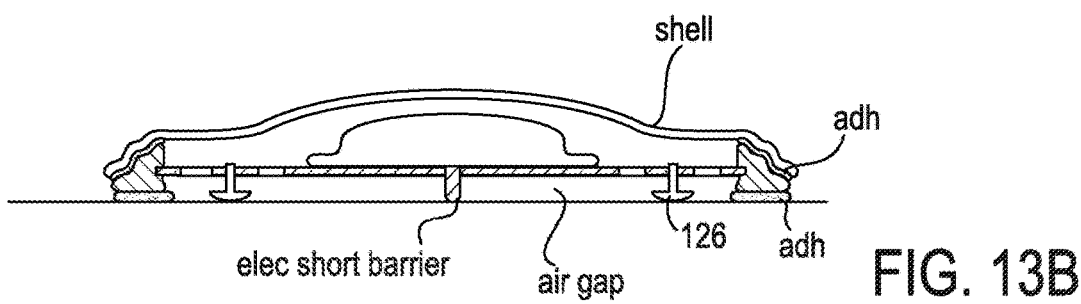

FIG. 13B shows a cross-section of the patch of FIG. 13A.

DETAILED DESCRIPTION

The following device features and design elements can be implemented into any device being adhered to the human body for a long-period of time, typically greater than 24 hours. As an example, the following device features and design elements can be used for long-term adhesion of a cardiac rhythm monitoring patch ("patch") to the chest of a person.

Referring to FIGS. 1 and 1A, a patch 100 for long term adhesion includes a housing 102. The housing 102 can be formed from any flexible, durable material, such as a biocompatible polymer, for example silicone. The housing 102 can include electronic components 108 therein. As shown in FIG. 2, the electronics 108 can include a printed circuit board 220, a battery 225, and a communications port mounted on the printed circuit board 220. The printed circuit board 220 can include analog circuits 210, digital circuits 215, and an activation or event notation button or switch 130. The electronics 108 can be used, for example, to record continuous physiological signals from a mammal wearing the patch 100. A system for continuously recording data is described further in co-owned U.S. application Ser. No. 11/703,428, filed Feb. 6, 2007, the entire contents of which are incorporated by reference herein.

As shown in FIGS. 1 and 1A, wings 104, 106 can be connected to the housing 102. The wings 104, 106 can be integral with the housing 102 and, in some embodiments, can be formed of the same material as the housing 102. The wings 104, 106 can be more flexible than the electronic components 108, which can be substantially rigid. An electrode 124, 126 can extend through a bottom surface of each wing 104, 106. The electrodes can be positioned to detect an ECG of a mammal wearing the patch 100 for processing by the electronics 108. For example, the electrodes can be more than 2 cm apart, such as more than 3 cm apart, for example at least 6 cm apart. The electrodes 124, 126 can be integral with the wings 104, 106 so as to be inseparable from the wings 104, 106 when the patch is in use.

For a patch 100 that is entirely flexible and can conform, stretch, and adapt to the movement and conditions of the chest underneath the device, adhesive can be placed over the entire surface of the device that is in contact with the body, except for areas where sensors, electronics, or others elements such as electrodes are interacting with the body related to the functioning of the device may be incorporated. Thus, as shown in FIG. 3, an adhesive layer 166 can coat the bottom of the patch 100 tor attachment to the skin, For a patch 100 in which there may be some areas that are not completely flexible and may not be able to stretch or contract (e.g., the electronics 1(8), adhesive may be excluded from the portion of the patch 100 underneath these areas. Thus, for example, the bottom surface 302 of the housing 102, which contains the electronics, can remain free from adhesive. As shown in FIG. 1A, by not coating adhesive on a bottom surface of the housing 102, the housing 102 can float above the adhered portions, allowing for increased flexibility of the patch, as will be discussed further below. Further, as shown in FIG. 3 the bottom surface of the electrodes 124, 126 can remain free of adhesive. For example, a ring 362 without adhesive can be formed around each electrode 124, 126 to separate the electrodes from the adhesive 164, The adhesive can be, for example, a pressure-sensitive adhesive, such as polyacrylate, polyisobutlene, or a polysiloxane. Alternatively, the adhesive can be a hydrocolloid which advantageously absorbs water.

The wings 104, 106 and the housing 102 can form a smooth, contiguous outer surface to the patch 100, As shown in FIG. 1A, when viewed from the top, the housing 102 and wings 104, 106 can together form an oblong substantially oval shape, Further, the housing 102 can have a thickness that is greater than the thickness of the wings 104, 106. The housing 102 and each of the wings 104, 106 when viewed in profile, can each form a dome with a height that is greater at the center than at the ends of the respective component, i.e. some or all of the components can be tapered at the ends and/or sides.

The electronics 108 can extend along only a portion of the distance between the electrodes 104, 106. For example, the electronics can occupy less than 90% of the distance between the electrodes, for example less than 80%. By having the electronics 108 in a relatively limited space between the electrodes 124, 126, the flexibility of the patch 100 can be increased The housing 102 can provide a watertight enclosure 110 for electronic components 108 of the patch 100, The electronics 108 can be unattached to the housing 102 such that the electronics 108 are free to move within the watertight enclosure 110. Allowing the relatively rigid electronics 108 to move freely within the flexible housing 102 advantageously enhances the overall flexibility of the patch 100, The wings 104, 106 can each have a watertight enclosure 114, 116 formed therein, which can be contiguous with the watertight enclosure 110 of the housing 102.

Wiring 120 or other suitable electrical connections can connect the electrodes 124, 126 with the electrical components 108 of the housing. In some embodiments, as shown in FIGS. 1B-1E, the contiguous nature of the enclosure 110 and the enclosures 114, 116 allows the wiring 120 to extend within the patch 100 from the electrodes 124, 126 to the electronic components 108. In other embodiments, one or more channels, tubes, or conduits are provided between the housing 102 and the wings 104, 106, to provide space for the wiring 120. The tube or channel may be straight or curved. In use, the wire 120 positioned in the enclosures 110, 114, 116 or in the tube or channel may move relative thereto in order to remain flexible within the housing. In one aspect, the flexible channels or tubes are formed within the device housing so that the housing, as it is being stretched, does not affect the ability of the components, such as wires, that may connect more rigid structures, to move or elongate.

As shown in FIG. 1, the wire 120 is straight with a direct line of connection between the electrodes 124, 126 and the electronics 108. FIG. 1 illustrates an embodiment where the length of the wires 120 connecting the electrodes 124, 126 to electronics 108 are about the same distance as the spacing between the electrode connection point on electronics 108 and the electrodes 124, 126. FIG. 1F also illustrates a straight line type connection where wire 120 length is nearly the same as the spacing between the electronics 108 and the electrodes 124, 126. However, as a patient moves, the patch 100 flexes along with patient movement. As shown in FIGS. 4B and 5C, patch flexion may be severe and is likely to occur during long term monitoring. In order to address the possible dislocation or breakage of the wire 120, the length or shape of the wire 120 may be selected to permit patch flexion to occur with little risk of wire 120 pulling from the electrode or electronics. Numerous alternatives are possible to compensate for patch flexion. Exemplary confirmations include undulations or zig-zags 231 as shown in FIG. 2B, coils 233 as shown in FIG. 2e, or a configuration that partially or fully wraps around an electrode. In some embodiments, other components, such as the circuit hoard or electrodes, can alternatively or additionally contain additional length to help accommodate stretch or displacement. When the patch 100 is attached to a mammal, the slack in the wiring 120 allows the patch 100 to flex while not placing stress on the wiring 120.

While the illustrated embodiments of FIGS. 1A-1D show only two wings and show the electrodes and electronics in a direct line in a approximate 180 degree alignment of electrode 124 to electronics 108 to electrode 126), other configurations are possible. For example, as shown in FIG. 1F, the wings 104, 106 are arranged in an orientation less than 180 degrees. In the illustrated embodiment, the angle formed by the electrodes and the electronics is about 135 degrees. Other ranges are possible so long as electrode spacing is provided to permit ECG monitoring. The orientation of the wings 104, 106 to the housing 102 also illustrates the use of an additional adhesive tab 105. Tab 105 is shown as a semicircular extension of the body 102. The bottom of tab 105 can include adhesives as described herein and is used to provide additional anchoring of the patch to the patient. The tab 105 may be formed in any of a number of different shapes such as rectangles, ovals, loops or strips. Further, in some embodiments, the tab 105 can function similar to a wing, e.g., include an electrode therethrough that connects to the electronics 108.

Referring to FIGS. 1A-1D and 2B-2C, a hinge portion 194,196 in the patch 100 can extend between each electrode 124, 126 and the electronics 108. The hinge portions 194, 196 can have a thickness less than the thickness of surrounding portions of the patch 100, For example, if the hinge portions 194, 196 are in the wings 104, 106, then the thickness can be less than adjacent portions of the wings. Likewise, the hinge portions 194, 196 can have a width less than adjacent portions of the patch 100, e.g., less than adjacent portions of the wings 104, 106. Alternatively, the hinged portion can be formed by the adjunct between a rigid portion, i.e. the electronics 108, and a more flexible portion, The hinged portion allows the patch 100 to bend between the housing 102 and wings 104, 106 to compensate for any movement caused by the patient. As shown in FIGS. 2B and 2C, the slack in the wiring 120 can be placed at or proximal to the hinge portions 194, 196 to allow for bending at the hinge portions 194, 196 without pulling or breaking the wiring 120.

Referring to FIGS. 4A and 4B, having adhesive on the bottom of the patch 100 except in the areas substantially around the electrodes and directly underneath the housing 102 can create a floating section 455 over the skin of the mammal to which the patch 100 is attached. The floating section 455 can house the more rigid or less flexible electronic components while the flexible wings 104, 106 can be adhered to the skin and provide the flexibility necessary to hold the patch 100 in place. As a result of this selective use of adhesive areas and non-adhesive areas, the limitation on device flexibility imposed by the less flexible floating section can he mitigated or reduced by hounding the floating section with one or more adhered flexible areas. The flexible sections can thus adhere to the body if the underlying portion of the body is stretched and/or contracted while the floating section is free to move above the skin, for example if the person wearing the device rolls over (as shown in FIG. 4A) or is involved in activities that can otherwise cause movement of the skin (as shown in FIG. 4B).

Referring back to FIGS. 1B-1E, each wing 104, 106 can include a material layer 214,216 between the adhesive 164, 166 and the wings 104, 106, The material layer 214,216 can be, for example, a polyester layer. The material layer 214, 216 can be attached to the patch 100 with a layer of adhesive 204,206, The adhesive 204, 206 can be the same as the adhesive 164, 166 or different. For example, the adhesive 204, 206 could be a silicone adhesive. The material layer 214 can serve as a barrier to prevent diffusion or migration of adhesive components, such as a tackifier, from the adhesive 164, 166 into the wings 104, 106 or housing 102. The material layer 214 can thus advantageously serve to maintain the strength of the adhesive 104, 106 over time.

Referring still to FIGS. 1B-1E, the patch 100 can further include a first flap 154 connected to the first wing 104 and a second flap 156 connected to the second wing 106. The flaps 154, 156 can both extend from a position on the wings 104, 106 medial to the electrodes to a position below the housing 102, such as below the electronics 108. The flaps 154, 156 can remain unattached to the housing 102. As a result, gaps 144, 146 can be formed between the flaps 154, 156 and the housing 102. The gaps can provide additional "floating" for the housing 102 and the relatively rigid components 108 contained therein.

In some embodiments, shown in FIG. 1B, the flaps 154, 156 can be attached to the wings 104, 106 with adhesive 134, 136. The adhesive 134, 136 can be the same as the adhesive 164, 166 or different. For example, the adhesive 134, 136 could be a silicone adhesive. In other embodiments, shown in FIGS. 1C-1E, the flaps 154, 156 can be integral with the wings 104, 106. For example, the flaps 154, 156 can be solvent welded to and/or formed during the molding process of the wings 104, 105 such that hinges 194, 196 form below the wings 104, 106. Additionally or alternatively, one or more of the flaps 154, 156 may be separably attached to the wings 104, 106. In some embodiments, shown in FIGS. 1B and 1C, the materials making up the flaps 154, 156 can extend all the way to the lateral edge of the patch 100. In other embodiments, shown in FIG. 1D, a flap can extend on each side of the electrodes, i.e. one flap can extend medially and the other laterally. In some embodiments, the lateral and medial—extending flaps are part of the same annular flap. In other embodiments, shown in FIG. 1E, the flaps and materials making up the flaps extend only from a position medial to the electrodes underneath the housing.

The Flaps 154, 156 may be positioned in virtually any relationship to the adhered flexible area such that, when attached in use, the attachment of the flap or flaps effectively counteracts the expected external forces acting on the device, specifically those forces that may dislodge the adhered flexible areas. Further, in embodiments such as that shown in FIG. 1F where there are more than two wings, there can be a flap corresponding to each additional wing.

The adhesive layers 164, 166 can coat all or a portion of the bottom of each of the flaps 154, 156. In some embodiments, the adhesive 164, 166 extends continuously from the bottom surface of the wings 104, 106 to the bottom surface of the flaps 154, 156, except for areas proximate to the electrodes 124, 126. Further, the top surface of the flaps 154, 156, i.e. the surface closest to the housing 102, can remain free of adhesive to ensure that the housing 102 remains floating. In some embodiments, the only portion of the patch 100 including adhesive for adhesion to the skin can be the flaps 154, 156.

Referring to FIGS. 5A-5C, the naps 154, 156, can provide hinge-like behavior for the patch 100, Thus, as shown in FIG. 5A, if the skin 501 is stretched or bent in a concave manner, the gaps 144, 146 between the flaps 154, 156 and the housing 102 can approach zero such that the patch 100 can sit substantially flat on the skin 501. As shown, the hinge portions 194, 196 between the housing 102 and wings 104, 106 can provide additional flexibility for concave bends by flattening as the patch 100 is stretched. In contrast, as shown in FIGS. 5B and 5C, as the skin 501 is bent in an increasingly convex manner, the gaps 144, 146 between the flaps 154, 156 and the housing 102 can increase, thereby allowing the flexible wings 104, 106 to remain adhered to the skin and the rigid housing 102 to float above skin. As shown, the hinge portions 194, 196 between the housing and the wings 104, 106 can provide additional flexibility for convex bends by folding inward as the patch 100 is bent.

When placed substantially flat on the skin 501, the patch 100 can have a height that extends no more than 2 cm off of the skin, such as no more than 1.5 cm off of the skin, when lying flat on the patient and no more than 4 cm, such as no more than cm off of the skin when floating above the skin. The relatively low height of the patch 100 can enhance long-term adhesion by reducing the potential for the patch] 00 to snag or rip off of the skin.

Advantageously, the flaps 154, 156 can function as anchors for adhesion that mitigates shear force. The flaps 154, 156 can provide a different direction for the acute and chronic forces being experienced by the device due to stretching, contraction, or torsion to be spread out over both the flap as well as the flexible adhesive areas. Further, by pre-aligning the orientation of the floating section, adhered flexible area and the flaps, the device may be better able to tolerate (i.e., remain attached to the body and in use) and/or tailor the interaction with the forces acting on the device in order to better withstand the acute or chronic forces being experienced by the device. Tailoring the response of the device to the expected forces is one Because the flaps can be used to counteract forces acting on a particular device, it is to be appreciated that the dimensions, flexibility, attachment technique, and/or orientation between a flap and another component may vary depending upon the purpose of a particular flap. Accordingly, a flap may have the same or different characteristics from another flap or component of the device. In one aspect, at least one flap is more flexible that the other flaps in a particular device. In another aspect, each of the flaps has similar flexibility. In still another aspect, at least one flap is more flexible than the device component to which it is attached or from which it originates. In still another aspect, at least one flap is less flexible than the device component to which it is attached or from which it originates.

Referring to FIGS. 6A and 6B, in one embodiment, the flaps 154, 156 may be augmented by a connector segment 607 used to join the flaps together. The connector segment 607 can extend below the housing 102, but remain unattached to the housing 102. As shown in FIG. 6A, the flaps 154, 156 and the connector 607 can together form a butterfly shape. In one embodiment, the connector segment 607 and the flaps 154, 156 are formed from a single piece of material. The connector segment 607 can be made of the same material as the flaps 154, 156 or of different material. In one embodiment, the bottom surface of the connector is covered with adhesive. In another embodiment, the bottom surface of the connector does not include any adhesive. Further, as shown in FIG. 6B, the connector segment 607 can be thicker in the middle, under the housing 102, than near the edges, i.e., closer to the electrodes. The variable thickness can help prevent the connector segment 607 from capturing moisture thereunder. The connector segment 607 can advantageously prevent the device from flipping when attached to the patient The connector segment 607 can include one or more holes 614, 616. In some configurations, the connector segment may trap moisture and/or inadvertently stick to the body. The holes 614, 616 can advantageously minimize the potential for undesired sticking or moisture collection. The size, shape and placement of the holes mitigate or reduce the collection of moisture and/or undesired adhesive still providing a connector with sufficient structural integrity (i.e. the connector allows the flaps to be connected to one another in order to prevent them from folding). Additionally or alternatively, the connector holes could also be made to preferentially allow forces to be distributed along certain axes of the connector in order to further maximize the ability of the device to adhere tong-term in the face of significant acute and chronic forces due to stretching, contraction, and torsion.

Adhesive can be selectively applied to the connector and/or naps to provide the desired body attachment locations depending upon the specific use of the device. For example, one piece of material including flaps and the connector can be adhered along two or more edges and/or with adhesive only covering certain areas, In another aspect, at least a portion of the skin-contacting surface of the unitary nap connector structure does not include any adhesive. Additionally or alternatively, the connector segment incorporating the flaps may be integral parts of the larger device housing (e.g. could be molded as part of the device housing or enclosure).

In some embodiments, the patch 100 can include one or more release liners to cover parts of the adhesive prior to adhesion. As is particular to devices having multiple adhesive areas and/or multiple adhesive components (i.e., flaps and flexible sections), the manner of applying the device may be specifically detailed in order to ensure that the device and the adhesive portions are properly engaged. In one particular aspect, the release liners are removed in a particular order to minimize the likelihood that the device adhesive is misapplied. For example, a portion of the adhesive may be exposed first and used to affix the device to the body, Thereafter, a second set of adhesive liners may be removed to expose and affix one or more flaps to the body, A stepwise adhesive exposure method may be implemented during device application such that elements, such as the one or more flaps do not fold on themselves, for example.

Breaking up the areas in which the adhesive is used to adhere the device, whether it be splitting it up to rigid areas, to create flaps, to create connector segments with holes, of any of the other techniques described above may also have benefits in terms of preventing moisture bridges that could act as conducting pathways between electrical sensing elements, such as electrodes. Bridges of moisture could short-circuit electrical connections and/or prevent the proper functioning of the device, particularly if the device has an electrical function, such as sensing via electrodes.

In some applications, a long-duration patch may experience excessive forces due to acute (quick and/or rapid) or chronic (slow and/or prolonged) contraction, stretching, or torsion. In such applications, the hinge points between a floating rigid section and flexible adhered sections may be modified in order to align with and counteract or mitigate the predominant direction of the force acting on the patch. In some device situations or configurations, the strength and direction of the acute or chronic force may be so strong that the forces imparted on the device adhesive surfaces or components may be distributed differently in addition to or as an alternative to the hinge described above.

Further, the device construction can be made in such a way that the housing is fashioned so that the axes of the housing are structured and placed along or against the direction of various forces, possibly during certain states, such as sleeping, so that the device itself can help counteract these forces and improve long-term adhesion.

Advantageously, the patch described herein can provide long-term adhesion to the skin. Having the various flexible portions and/or hinged portions can compensate for stressed caused as the skin stretches or bends, while allowing the rigid portion to float about the skin. As a result, the devices described herein can adhere to the skin substantially continuously tor more than 24 hours, such as greater than 3 days, for example, greater than 7 days, greater than 14 days, or greater than 21 days.

Another mechanism for adhering a patch to the skin long-term is described with respect to FIGS. 7-10. As shown in the embodiments of FIGS. 7-10, one or more parts of the patch are used in a temporary fashion in order to improve adhesion. The adhesive used in the embodiments described below can include a hydrocolloid or a pressure-sensitive adhesive, such as polyacrylate, polyisobutylenes, or polysiloxane.

In one embodiment, shown in FIGS. 7A and 7B, the patch 700 can be surrounded with an adhesive 760 having multiple covers 701, 703, 705 thereon that can be peeled away in a sequence to expose strips of adhesive 760 underneath. The covers 701,703,705 can be concentric with one another and be configured to be pulled off separately and sequentially starting from the inside of the patch 700. Each additional exposed area of adhesive 760 can increase the adhesion life of the patch 700. Although only three covers are shown in FIG. 7A, other numbers, such as 2, 4, 5, or more are possible. Further, each electrode 124, 126 of the patch 700 can include a barrier 714,716 to protect the electrodes 124, 126 from shortage.

In another embodiment, shown in FIGS. 8A and 8B, each electrode 124, 126 can be surrounded by a patch of adhesive 864, 866. Accordingly, a set of covers 801, 803, 805, 807 can be positioned sequentially around each of the electrodes 124, 126 over the adhesive 864, 866. The covers 801, 803, 805, 807 can be concentric with one another and be configured to be pulled off sequentially starting from the inside. Each additional exposed strip of adhesive 864, 866 can increase the adhesion life of the patch 100. Although only four covers are shown in FIG. 8A, other numbers, such as 2, 3, 5, or more are possible. Further, each electrode 124, 126 of the patch 800 can include a barrier 814, 816 to protect from shortage.

Referring to FIGS. 9A-9B, in other embodiments, shells or layers 901,902,903 can extend over all or a portion of the patch 900. Each layer 901,902,903 can include a strip of adhesive 962 on the bottom surface and an adhesion guard 982 protecting the adhesive. As shown in FIG. 913, as the patch 900 is worn over a period of time, the layers 901, 902, 903 can be sequentially removed. As a new layer is exposed, the adhesive guard 982 of that layer can be peeled away such that the adhesive 962 of the new layer can be used to adhere the patch 900 to the skin, In a similar embodiment, referring to FIGS. 10A-10B, each of the layers 1001, 1002, 1003 can include multiple portions of adhesive to help adhere the layer to both the skin and the patch itself. As with the embodiments of FIGS. 7-8, the number of layers in the embodiments of FIGS. 9 and 10 can vary. For example, there can be 2, 3, 4, or 5 or more layers.

In some embodiments, the layers or covers of the embodiments described herein can be added to the device over time to improve adhesion. Further, the multiple layers or covers of the embodiments described herein can be partially overlapped. Further, in some embodiments, the strips of adhesive can be overlapped.

Advantageously, the use of multiple covers or layers can assist in the adhesive performance of a base or core device because the added surface area or adhesive force of the combined outer layer aids in preventing layer pull away and/or may act to spread forces being experienced away from the core device by spreading those forces over a larger area.

Referring to FIGS. 11 and 12, an open cell structured support 1330 or porous foam can be used to support a more rigid or less flexible portion 1302 of the patch 1300, As shown in FIG. 11, the open cell structured support 1330 can fully fill an area below the rigid portion 1302. Alternatively, as shown in FIG. 12, the open cell structured support 1330 can be an annular shape or have some other configuration that includes spaces between adjacent portions of the support. The open cell structured support 1302 may be attached to both the skin and to the rigid portion, to only the rigid portion, or to only the skin. Because of the open cell structure of the support, the flexible movement of the skin can be absorbed by the structure entirely or partially such that the rigid portion does not impact or has a reduced impact on the ability of the device to accommodate movement and remain affixed. In addition, the open cell support may have a thickness selected to enhance patient comfort so that the more rigid portion of a device does not push against the skin. In one aspect, the open cell structure is a biocompatible foam material. In another aspect, the open cell material is positioned between an electronics module on the device and the skin when worn by a patient. The open cell support can advantageously absorb fluids to keep the electrodes from shorting.

Referring to FIG. 13, the patch can have a shell design. Adhesive can be placed on the perimeter edge of the bottom ring. The circuit board and electrode unit can be dropped into the bottom ring, and a shell can be dropped on top of the circuit board and electrode. The perimeter adhesive can create a watertight chamber therein.

The shape of a particular electronic device embodiment may vary. The shape, footprint, perimeter or boundary of the device may be a circle or circular (see FIG. 13A), an oval (see FIG. 1A, 2A), a triangle or generally triangular (see FIG. 1F) or a compound curve. Examples of a device embodiments having a compound curve shape are shown in FIGS. 2B, 2B, 3, 6A, 7A, and 8A. In some embodiments, the compound curve includes one or more concave curves and one or more convex curves. FIG. 3 illustrates a device having a convex surface along the top (where reference 102 indicates), a concave surface along the bottom and convex shaped edges around the electrodes 124, 126. FIGS. 2B and 2C illustrate a device embodiment having a convex shape on either side of the electronics 108 and around the electrodes 124, 126. The convex shapes are separated by a concave portion. The concave portion is between the convex portion on the electronics and the convex portion on the electrodes, In some embodiments, the concave portion corresponds at least partially with a hinge, hinge region or area of reduced.

While described in the context of a heart monitor, the device adhesion improvements described herein are not so limited. The improvement described in this application may be applied to any of a wide variety of conventional physiological data monitoring, recording and/or transmitting devices. The improved adhesion design features may also he applied to conventional devices useful in the electronically controlled and/or time released delivery of pharmacological agents or blood testing, such as glucose monitors or other blood testing devices. As such, the description, characteristics and functionality of the components described herein may be modified as needed to include the specific components of a particular application such as electronics, antenna, power supplies or charging connections, data ports or connections for down loading or off loading information from the device, adding or offloading fluids from the device, monitoring or sensing elements such as electrodes, probes or sensors or any other component or components needed in the device specific function. In addition or alternatively, devices described herein may be used to detect, record, or transmit signals or information related to signals generated by a body including but not limited to one or more of EKG, EEG, and/or EMG.

What is claimed is:

1. A body-worn device configured to monitor cardiac rhythm data, the body-worn device comprising:
    a housing formed from a polymer material, in which at least some substantially rigid electronic components are disposed, including a printed circuit board and a battery connected to the printed circuit board;
    a flexible layer, wherein the flexible layer is adhered to the housing, the flexible layer is made of material that is different from the polymer material of the housing, the flexible layer is more flexible than the housing, a portion of a skin contacting surface of the flexible layer is configured to bend independently from the housing, allowing for a gap between the housing and the flexible layer to facilitate adherence of the flexible layer to a body of a patient accommodating different positions and movements of the patient;
    a first electrode positioned on a bottom surface of the flexible layer at a distance from the housing, wherein the first electrode is embedded in the flexible layer and is electrically connected via a flexible material to the printed circuit board, and at least a portion of the electrical connection extends linearly between the first electrode and the printed circuit board, and the flexible layer comprises a first layer and a second layer, wherein the first layer is positioned over the first electrode and extends beyond a boundary of the first electrode, and wherein the second layer is positioned over the first layer extends horizontally beyond a boundary of the first layer;
    a second electrode positioned on the bottom of the device, wherein the first electrode and second electrode are more than 6 cm apart, the first electrode, the second electrode, the electrical connection, and the substantially rigid electronic components are centered in a line on the device, a portion of the electrical connection that extends linearly between the first electrode and a connection point at the printed circuit board shorter than the distance between the first electrode and second electrode, and the substantially rigid electronic components occupy less than 80% of the distance between the first and second electrodes, thereby increasing the ability of the flexible layer to conform to the patient during movement of the patient; and
    a removable release liner overlaps an electrode and an adhesive on a bottom surface of the flexible layer, the removable release liner configured to expose the electrode and the adhesive for connection to a skin of the patient when removed, and the removable release liner extending horizontally beyond a boundary of the flexible layer.

2. The body-worn device of claim 1, wherein the housing is substantially rigid.

3. The body-worn device of claim 1, further comprising a connecting adhesive layer adhering the first layer to the second layer.

4. The body-worn device of claim 1, wherein the adhesive comprises a hydrocolloid adhesive.

5. The body-worn device of claim 1, wherein the adhesive comprises a pressure-sensitive adhesive.

6. The body-worn device of claim 1, wherein the adhesive extends at least partially below the housing.

7. The body-worn device of claim 1, wherein the adhesive does not extend beneath the housing.

8. The body-worn device of claim 1, wherein the printed circuit board comprises a data collection circuit configured to collect cardiac rhythm data from the patient.

9. The body-worn device of claim 8, wherein the electrical connection extends linearly between the first electrode and the data collection circuit of the printed circuit board.

10. The body-worn device of claim 1, wherein the housing is configured to remain connected to the flexible layer when the housing is tilted at an angle relative to the bottom surface of the flexible layer in response to movement of the patient.

11. The body-worn device of claim 1, further comprising a hinge portion adjacent the housing.

12. The body-worn device of claim 1, wherein the housing provides a watertight enclosure for the printed circuit board.

13. The body-worn device of claim 1, wherein the first electrode is positioned in a wing that extends away from the housing.

14. The body-worn device of claim 1, wherein the adhesive can adhere to the skin of the patient for more than 24 hours.

15. The body-worn device of claim 14, wherein the adhesive can adhere to the skin of the patient for more than 3 days.

16. The body-worn device of claim 1, wherein the flexible layer comprises a third layer.

17. The body-worn device of claim 16, wherein the third layer is between the first layer and the second layer.

18. The body-worn device of claim 16, wherein the third layer extends beyond the boundary of the first layer.

19. The body-worn device of claim 1, wherein the flexible layer is thinner at the edges than in the center.

20. The body-worn device of claim 19, wherein the varying thickness of the flexible layer prevents the flexible layer from capturing moisture.

\* \* \* \* \*